United States Patent
Yeung et al.

(10) Patent No.: US 8,507,683 B2
(45) Date of Patent: Aug. 13, 2013

(54) COMPOUNDS FOR THE TREATMENT OF HEPATITIS C

(75) Inventors: Kap-Sun Yeung, Madison, CT (US); John F. Kadow, Wallingford, CT (US); Rajesh Onkardas Bora, Bangalore (IN); Kumaravel Selvakumar, Bangalore (IN)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 13/310,863

(22) Filed: Dec. 5, 2011

(65) Prior Publication Data

US 2012/0309770 A1    Dec. 6, 2012

Related U.S. Application Data

(60) Provisional application No. 61/421,448, filed on Dec. 9, 2010.

(51) Int. Cl.
*C07D 471/04* (2006.01)
*A61K 31/437* (2006.01)

(52) U.S. Cl.
USPC .......................... 546/121; 514/300

(58) Field of Classification Search
USPC .......................... 546/121; 514/300
See application file for complete search history.

(56) References Cited

FOREIGN PATENT DOCUMENTS

| WO | WO 2004/041201 | 5/2004 |
|---|---|---|
| WO | WO 2009/137500 | 11/2009 |
| WO | WO 2010/030592 | 3/2010 |
| WO | WO 2010030592 A1 * | 3/2010 |
| WO | WO 2011/112769 | 9/2011 |

\* cited by examiner

*Primary Examiner* — Jeffrey S. Lundgren
*Assistant Examiner* — Michael Schmitt
(74) *Attorney, Agent, or Firm* — James Epperson

(57) ABSTRACT

The disclosure provides compounds of formula I, including their salts, as well as compositions and methods of using the compounds. The compounds have activity against hepatitis C virus (HCV) and may be useful in treating those infected with HCV.

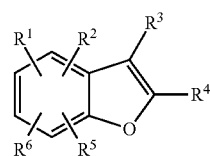

6 Claims, No Drawings

COMPOUNDS FOR THE TREATMENT OF HEPATITIS C

CROSS REFERENCE TO RELATED APPLICATIONS

This patent application claims the benefit of U.S. provisional patent application No. 61/421,448 filed Dec. 9, 2010.

BACKGROUND OF THE INVENTION

The disclosure generally relates to the novel compounds of formula I, including their salts, which have activity against hepatitis C virus (HCV) and are useful in treating those infected with HCV. The disclosure also relates to compositions and methods of using these compounds.

Hepatitis C virus (HCV) is a major human pathogen, infecting an estimated 170 million persons worldwide—roughly five times the number infected by human immunodeficiency virus type 1. A substantial fraction of these HCV infected individuals develop serious progressive liver disease, including cirrhosis and hepatocellular carcinoma (Lauer, G. M.; Walker, B. D. N. Engl. J. Med. 2001, 345, 41-52).

HCV is a positive-stranded RNA virus. Based on a comparison of the deduced amino acid sequence and the extensive similarity in the 5'-untranslated region, HCV has been classified as a separate genus in the Flaviviridae family. All members of the Flaviviridae family have enveloped virions that contain a positive stranded RNA genome encoding all known virus-specific proteins via translation of a single, uninterrupted, open reading frame.

Considerable heterogeneity is found within the nucleotide and encoded amino acid sequence throughout the HCV genome. At least six major genotypes have been characterized, and more than 50 subtypes have been described. The major genotypes of HCV differ in their distribution worldwide, and the clinical significance of the genetic heterogeneity of HCV remains elusive despite numerous studies of the possible effect of genotypes on pathogenesis and therapy.

The single strand HCV RNA genome is approximately 9500 nucleotides in length and has a single open reading frame (ORF) encoding a single large polyprotein of about 3000 amino acids. In infected cells, this polyprotein is cleaved at multiple sites by cellular and viral proteases to produce the structural and non-structural (NS) proteins. In the case of HCV, the generation of mature non-structural proteins (NS2, NS3, NS4A, NS4B, NS5A, and NS5B) is effected by two viral proteases. The first one is believed to be a metalloprotease and cleaves at the NS2-NS3 junction; the second one is a serine protease contained within the N-terminal region of NS3 (also referred to as NS3 protease) and mediates all the subsequent cleavages downstream of NS3, both in cis, at the NS3-NS4A cleavage site, and in trans, for the remaining NS4A-NS4B, NS4B-NS5A, NS5A-NS5B sites. The NS4A protein appears to serve multiple functions, acting as a cofactor for the NS3 protease and possibly assisting in the membrane localization of NS3 and other viral replicase components. The complex formation of the NS3 protein with NS4A seems necessary to the processing events, enhancing the proteolytic efficiency at all of the sites. The NS3 protein also exhibits nucleoside triphosphatase and RNA helicase activities. NS5B (also referred to as HCV polymerase) is a RNA-dependent RNA polymerase that is involved in the replication of HCV. The HCV NS5B protein is described in "Structural Analysis of the Hepatitis C Virus RNA Polymerase in Complex with Ribonucleotides (Bressanelli; S. et al., Journal of Virology 2002, 3482-3492; and Defrancesco and Rice, Clinics in Liver Disease 2003, 7, 211-242.

Currently, the most effective HCV therapy employs a combination of alpha-interferon and ribavirin, leading to sustained efficacy in 40% of patients (Poynard, T. et al. Lancet 1998, 352, 1426-1432). Recent clinical results demonstrate that pegylated alpha-interferon is superior to unmodified alpha-interferon as monotherapy (Zeuzem, S. et al. N Engl. J. Med. 2000, 343, 1666-1672). However, even with experimental therapeutic regimens involving combinations of pegylated alpha-interferon and ribavirin, a substantial fraction of patients do not have a sustained reduction in viral load. Thus, there is a clear and important need to develop effective therapeutics for treatment of HCV infection.

HCV-796, an HCV NS5B inhibitor, showed an ability to reduce HCV RNA levels in patients. The viral RNA levels decreased transiently and then rebounded during dosing when treatment was with the compound as a single agent but levels dropped more robustly when combined with the standard of care which is a form of interferon and ribavirin. The development of this compound was suspended due to hepatic toxicity observed during extended dosing of the combination regimens. U.S. Pat. No. 7,265,152 and the corresponding PCT patent application WO2004/041201 describe compounds of the HCV-796 class. Other compounds have been disclosed, see for example, WO2009/101022.

The invention provides technical advantages, for example, the compounds are novel and are effective against hepatitis C. Additionally, the compounds provide advantages for pharmaceutical uses, for example, with regard to one or more of their mechanism of action, binding, inhibition efficacy, target selectivity, solubility, safety profiles, or bioavailability.

DESCRIPTION OF THE INVENTION

One aspect of the invention is a compound of formula I,

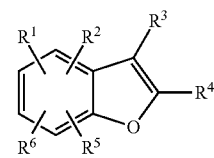

where:

$R^1$ is phenyl or pyridinyl and is substituted with 0-3 substituents selected from the group consisting of halo, alkyl, haloalkyl, hydroxyalkyl, alkoxyalkyl, alkoxy, hydroxyalkyloxy, and alkoxyalkyloxy, and is also substituted with 1 CON($R^9$)($R^{10}$) substituent;

$R^2$ is hydrogen, halo, or alkyl;

$R^3$ is CONHCH$_3$;

$R^4$ is phenyl that is independently substituted with 0-2 halo or methoxy or is para substituted with X—Ar$^1$;

$R^5$ and $R^6$ are independently hydrogen, alkyl, halo, N($R^7$)($R^8$), or alkylsulfonyl;

$R^7$ and $R^8$ are independently hydrogen, alkyl, hydroxyalkyl, alkoxyalkyl, alkylsulfonyl, or alkylsulfonylalkyl;

or N($R^7$)($R^8$) taken together is azetidinyl, pyrrolidinyl, piperidinyl, or piperazinyl, and is substituted with 0-2 substituents selected from alkyl, hydroxyalkyl, or hydroxy;

$R^9$ is hydrogen;
$R^{10}$ is

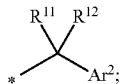

$R^{11}$ and $R^{12}$ taken together is —$CH_2OCH_2$—, —$OCH_2CH_2$—, —$CH_2OCH_2CH_2$—, —$OCH_2CH_2CH_2$—, —$CH_2OCH_2CH_2CH_2$—, —$CH_2CH_2OCH_2CH_2$—(thus forming an oxetanyl, dihydrofuranyl, or dihydropyranyl ring);

X is —O— or —NH—;

$Ar^1$ is phenyl or para-halophenyl; and $Ar^2$ is phenyl, pyridinyl, pyrazolyl, isoxazolyl, imidazolyl, oxazolyl, thiazolyl, oxadiazolyl, oxadiathiazolyl, triazolyl, tetrazolyl, pyrazinyl, or pyrimidinyl, and is substituted with 0-3 substituents selected from halo, alkyl, or dialkylamino;

or a pharmaceutically acceptable salt thereof.

Another aspect of the invention is a compound of formula I where:

$R^1$ is phenyl substituted with 0-2 substituents selected from the group consisting of halo, alkyl, or alkoxy, and is also substituted with 1 $CON(R^9)(R^{10})$ substituent;

$R^2$ is hydrogen or fluoro;

$R^3$ is $CONHCH_3$ $R^4$ is phenyl that is para substituted with fluoro;

$R^5$ and $R^6$ are hydrogen;

$R^9$ is hydrogen;

$R^{10}$ is

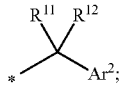

$R^{11}$ and $R^{12}$ taken together is —$CH_2OCH_2$— (thus forming an oxetanyl ring); and $Ar^2$ is phenyl, pyridinyl, or pyrimidinyl and is substituted with 0-3 substituents selected from halo or alkyl;

or a pharmaceutically acceptable salt thereof.

Another aspect of the invention is a compound of formula I where $R^1$ is phenyl substituted with 0-2 substituents selected from the group consisting of methyl, fluoro, and methoxy, and is also substituted with 1 $CON(R^9)(R^{10})$ substituent; $R^2$ is F; $R^3$ is $CONHCH_3$; $R^5$ and $R^6$ are hydrogen; $R^9$ is hydrogen; $R^{10}$ is

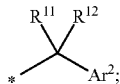

$R^{11}$ and $R^{12}$ taken together is —$CH_2OCH_2$— (thus forming an oxetanyl ring); and $Ar^2$ is phenyl, pyridinyl, or pyrimidinyl; or a pharmaceutically acceptable salt thereof.

Another aspect of the invention is a compound of formula I where $R^1$ is phenyl substituted with 1 $CON(R^9)(R^{10})$ substituent and also substituted with 0-2 halo, alkyl, or alkoxy substituents.

Another aspect of the invention is a compound of formula I where $R^4$ is phenyl or monofluorophenyl.

Another aspect of the invention is a compound of formula I where $R^{11}$ and $R^{12}$ taken together is —$CH_2OCH_2$—, —$OCH_2CH_2$—, —$CH_2OCH_2CH_2$—, —$OCH_2CH_2CH_2$—, —$OCH_2CH_2CH_2CH_2$—, —$CH_2OCH_2CH_2CH_2$—, —$CH_2CH_2OCH_2CH_2$— (thus forming an oxetanyl, dihydrofuranyl, or dihydropyranyl ring);

Another aspect of the invention is a compound of formula I where $R^{11}$ and $R^{12}$ taken together is —$CH_2OCH_2$— (thus forming an oxetanyl ring);

Another aspect of the invention is a compound of formula I where $Ar^1$ is phenyl.

Another aspect of the invention is a compound of formula I where $Ar^2$ is phenyl or pyridinyl.

Any scope of any variable, including $R^1, R^2, R^3, R^4, R^5, R^6, R^7, R^8, R^9, R^{10}, R^{11}, R^{12}, X, Ar^1,$ or $Ar^2$ can be used independently with the scope of any other instance of a variable.

Unless specified otherwise, these terms have the following meanings. "Halo" means fluoro, chloro, bromo, or iodo. "Alkyl" means a straight or branched alkyl group composed of 1 to 6 carbons. "Alkenyl" means a straight or branched alkyl group composed of 2 to 6 carbons with at least one double bond. "Cycloalkyl" means a monocyclic ring system composed of 3 to 7 carbons. "Hydroxyalkyl," "alkoxy" and other terms with a substituted alkyl moiety include straight and branched isomers composed of 1 to 6 carbon atoms for the alkyl moiety. "Halo" includes all halogenated isomers from monohalo substituted to perhalo substituted in substituents defined with halo, for example, "Haloalkyl" and "haloalkoxy", "halophenyl", "halophenoxy." "Aryl" means a monocyclic or bicyclic aromatic hydrocarbon groups having 6 to 12 carbon atoms, or a bicyclic fused ring system wherein one or both of the rings is a phenyl group. Bicyclic fused ring systems consist of a phenyl group fused to a four- to six-membered aromatic or non-aromatic carbocyclic ring. Representative examples of aryl groups include, but are not limited to, indanyl, indenyl, naphthyl, phenyl, and tetrahydronaphthyl. "Heteroaryl" means a 5 to 7 membered monocyclic or 8 to 11 membered bicyclic aromatic ring system with 1-5 heteroatoms independently selected from nitrogen, oxygen, and sulfur. Parenthetic and multiparenthetic terms are intended to clarify bonding relationships to those skilled in the art. For example, a term such as ((R)alkyl) means an alkyl substituent further substituted with the substituent R. Substituents which are illustrated by chemical drawing to bond at variable positions on a multiple ring system (for example a bicyclic ring system) are intended to bond to the ring where they are drawn to append. For example, substituents $R^1$ and $R^2$ of formula IV are intended to bond to the benzene ring of formula IV and not to the thiophene ring.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, camsylate, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention possess asymmetric carbon atoms. The invention includes all stereoisomeric forms, including enantiomers and diastereomers as well as mixtures of stereoisomers such as racemates. Some stereoisomers can be made using methods known in the art. Stereoisomeric mixtures of the compounds and related intermediates can be separated into individual isomers according to methods commonly known in the art. The use of wedges or hashes in the depictions of molecular structures in the following schemes and tables is intended only to indicate relative stereochemistry, and should not be interpreted as implying absolute stereochemical assignments.

The invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

Biological Methods

The compound demonstrated activity against HCV NS5B as determined in the following HCV RdRp assays.

HCV NS5B RdRp Cloning, Expression, and Purification. The cDNA encoding the NS5B protein of HCV, genotype 1b, was cloned into the pET21a expression vector. The protein was expressed with an 18 amino acid C-terminal truncation to enhance the solubility. The *E. coli* competent cell line BL21 (DE3) was used for expression of the protein. Cultures were grown at 37° C. for ~4 hours until the cultures reached an optical density of 2.0 at 600 nm. The cultures were cooled to 20° C. and induced with 1 mM IPTG. Fresh ampicillin was added to a final concentration of 50 µg/mL and the cells were grown overnight at 20° C.

Cell pellets (3 L) were lysed for purification to yield 15-24 mgs of purified NS5B. The lysis buffer consisted of 20 mM Tris-HCl, pH 7.4, 500 mM NaCl, 0.5% triton X-100, 1 mM DTT, 1 mM EDTA, 20% glycerol, 0.5 mg/ml lysozyme, 10 mM $MgCl_2$, 15 ug/ml deoxyribonuclease I, and Complete TM protease inhibitor tablets (Roche). After addition of the lysis buffer, frozen cell pellets were resuspended using a tissue homogenizer. To reduce the viscosity of the sample, aliquots of the lysate were sonicated on ice using a microtip attached to a Branson sonicator. The sonicated lysate was centrifuged at 100,000×g for 30 minutes at 4° C. and filtered through a 0.2 µm filter unit (Corning).

The protein was purified using two sequential chromatography steps: Heparin sepharose CL-6B and polyU sepharose 4B. The chromatography buffers were identical to the lysis buffer but contained no lysozyme, deoxyribonuclease I, $MgCl_2$ or protease inhibitor and the NaCl concentration of the buffer was adjusted according to the requirements for charging the protein onto the column. Each column was eluted with a NaCl gradient which varied in length from 5-50 column volumes depending on the column type. After the final chromatography step, the resulting purity of the enzyme is >90% based on SDS-PAGE analysis. The enzyme was aliquoted and stored at −80° C.

Standard HCV NS5B RdRp Enzyme Assay. HCV RdRp genotype 1b assays were run in a final volume of 60 µl in 96 well plates (Costar 3912). The assay buffer is composed of 20 mM Hepes, pH 7.5, 2.5 mM KCl, 2.5 mM $MgCl_2$, 1 mM DTT, 1.6 U RNAse inhibitor (Promega N2515), 0.1 mg/ml BSA (Promega R3961), and 2% glycerol. All compounds were serially diluted (3-fold) in DMSO and diluted further in water such that the final concentration of DMSO in the assay was 2%. HCV RdRp genotype 1b enzyme was used at a final concentration of 28 nM. A polyA template was used at 6 nM, and a biotinylated oligo-dT12 primer was used at 180 nM final concentration. Template was obtained commercially (Amersham 27-4110). Biotinylated primer was prepared by Sigma Genosys. $^3$H-UTP was used at 0.6 µCi (0.29 µM total UTP). Reactions were initiated by the addition of enzyme, incubated at 30° C. for 60 min, and stopped by adding 25 µL of 50 mM EDTA containing SPA beads (4 µg/µL, Amersham RPNQ 0007). Plates were read on a Packard Top Count NXT after >1 hr incubation at room temperature.

Modified HCV NS5B RdRp Enzyme Assay. An on-bead solid phase homogeneous assay was also used to assess NS5B inhibitors (Wang Y-K, Rigat K, Roberts S, and Gao M (2006) Anal Biochem, 359: 106-111). The assay is a modification of the standard assay described above and was used in a 96-well or a 384-well format. The biotinylated oligo dT12 primer was captured on streptavidin-coupled beads (SPA beads (GE, RPNQ0007) or imaging beads (GE, RPNQ0261) by mixing primer and beads in buffer and incubating at room temperature for three hours. Unbound primer was removed after centrifugation. The primer-bound beads were resuspended in 3× reaction buffer (40 mM Hepes buffer, pH 7.5, 7.5 mM $MgCl_2$, 7.5 mM KCl, dT primer coupled beads, poly A template, $^3$H-UTP, and RNAse inhibitor (Promega N2515). Compounds were serially diluted 1:3 in DMSO and aliquoted into assay plates. Equal volumes (20 µL for 96-well assay and 10 µL for 384-well assay) of water, 3× reaction mix, and enzyme in 20 mM Hepes buffer, pH 7.5, 0.1 mg/ml BSA were added to the diluted compound on the assay plate. Final concentration of components in 96-well assay: 0.36 nM template, 15 nM primer, 0.43 µM (1 µCi)$^3$H-UTP, 0.08 U/µL RNAse inhibitor, 7 nM NS5B enzyme, 0.033 mg mL BSA, and 2 µg/µL beads, 20 mM Hepes buffer, pH 7.5, 2.5 mM $MgCl_2$, 2.5 mM KCl, 2% DMSO. Final concentration of components in 384-well assay: 0.2 nM template, 15 nM primer, 0.29 µM $^3$H-UTP (0.3 µCi), 0.08 U/µL RNAse inhibitor, 7 nM NS5B enzyme, 0.033 mg/mL BSA, and 0.33 µg/µL beads, 20 mM Hepes buffer, pH 7.5, 2.5 mM $MgCl_2$, 2.5 mM KCl, 2% DMSO.

Reactions were allowed to proceed for 4 hours at 30° C. and terminated by the addition of 50 mM EDTA (10 µL). After incubating for at least 15 minutes, plates were read on a Packard NXT Topcount or Amersham LEADseeker multimodality imaging system.

$IC_{50}$ values for compounds were determined using seven different [I]. $IC_{50}$ values were calculated from the inhibition using the formula y=A+((B−A)/(1+((C/x)^D))).

Cell Lines. The cell lines used to evaluate compounds consist of a human hepatocyte derived cell line (Huh-7) that constitutively expresses a genotype 1a or 1b HCV replicon containing a *Renilla* luciferase reporter gene. These cells were maintained in Dulbecco's modified Eagle medium (DMEM) containing 10% FBS, 100 U/mL penicillin/streptomycin and 1.0 mg/mL G418.

HCV Replicon Luciferase Assay. To evaluate compound efficacy, HCV replicon cells were seeded in 96-well plates in DMEM containing 10% FBS at a cell density of $10^4$/well. Following incubation at 37° C. overnight, compounds serially diluted in DMSO were added to the cell plates. Alternatively, titrated compounds were transferred to sterile 384-well tissue-culture treated plates and the plates seeded with 50 μL of cells at a density of $2.4 \times 10^3$ cells/well in DMEM containing 4% FCS (final DMSO concentration at 0.5%). After 3 days incubation at 37° C., cells were analyzed for *Renilla* Luciferase activity using the EnduRen substrate (Promega cat #E6485) according to the manufacturer's directions. Briefly, the EnduRen substrate was diluted in DMEM and then added to the plates to a final concentration of 7.5 μM. The plates were incubated for at least 1 h at 37° C. then read on a TopCount NXT Microplate Scintillation and Luminescence Counter (Packard) or Viewlux Imager (PerkinElmer) using a luminescence program. The 50% effective concentration ($EC_{50}$) was calculated using the exponential form of the median effect equation where $EC_{50}=100-[(\delta F_{inh}/\delta F_{con}) \times 100]$.

To assess cytotoxicity of compounds, Cell Titer-Blue (Promega) was added to the EnduRen-containing plates and incubated for at least 4 hrs at 37° C. The fluorescence signal from each well was read using a Cytoflour 400 (PE Biosystems) or Viewlux Imager. All $CC_{50}$ values were calculated using the median effect equation.

Representative data for a compound is reported in Table 1.

TABLE 1

| Structure | $IC_{50}$ (μM) | *$EC_{50}$ (μM) |
|---|---|---|
| 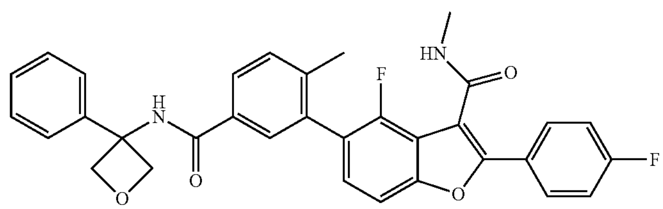 [SMILES: CNC(=O)c1c(-c2ccc(F)cc2)oc2ccc(-c3cc(C(=O)NC4(c5ccccc5)COC4)ccc3C)c(F)c12] | 0.057 | 0.004 |
| 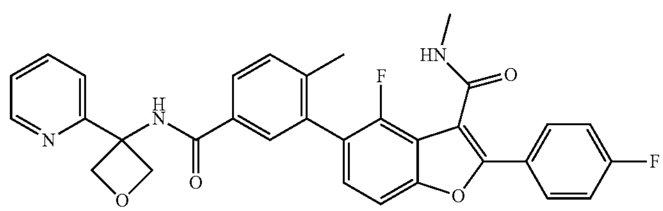 [SMILES: CNC(=O)c1c(-c2ccc(F)cc2)oc2ccc(-c3cc(C(=O)NC4(c5ccccn5)COC4)ccc3C)c(F)c12] | 0.024 | 0.024[1] |
| 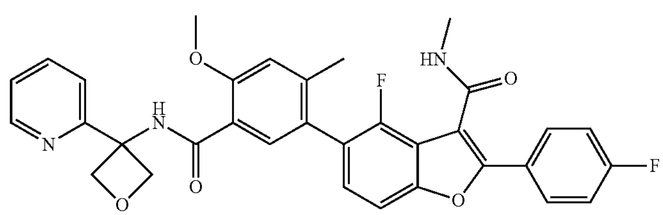 [SMILES: CNC(=O)c1c(-c2ccc(F)cc2)oc2ccc(-c3cc(C(=O)NC4(c5ccccn5)COC4)c(OC)cc3C)c(F)c12] | 0.017 | 0.008 |
| 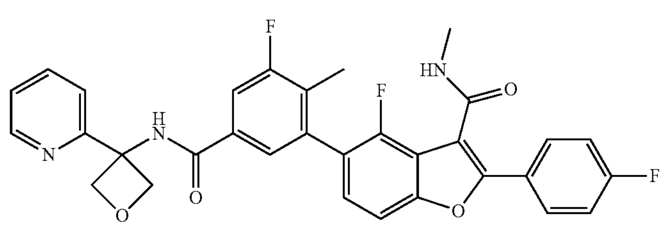 [SMILES: CNC(=O)c1c(-c2ccc(F)cc2)oc2ccc(-c3cc(C(=O)NC4(c5ncccn5)COC4)cc(F)c3C)c(F)c12] | 0.016 | 0.006 |
| 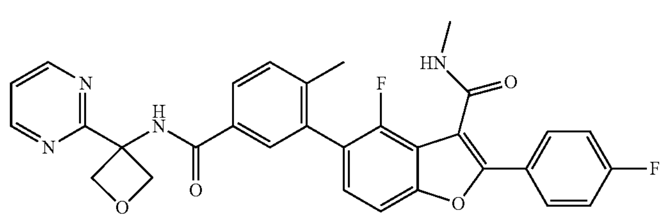 | 0.010 | 0.015 |

TABLE 1-continued

| Structure | IC$_{50}$ (μM) | *EC$_{50}$ (μM) |
|---|---|---|
| [structure] | 0.022 | 0.012 |
| [structure] | 0.006 | 0.012 |
| [structure] | | |

*1b genotype unless noted.
[1]1a genotype used for replicon data.

Pharmaceutical Compositions and Methods of Treatment

The compounds demonstrate activity against HCV NS5B and can be useful in treating HCV and HCV infection. Therefore, another aspect of the invention is a composition comprising a compound, or a pharmaceutically acceptable salt thereof, and a pharmaceutically acceptable carrier.

Another aspect of the invention is a composition further comprising a compound having anti-HCV activity.

Another aspect of the invention is a composition where the compound having anti-HCV activity is an interferon or a ribavirin. Another aspect of the invention is where the interferon is selected from interferon alpha 2B, pegylated interferon alpha, consensus interferon, interferon alpha 2A, interferon lambda, and lymphoblastoid interferon tau.

Another aspect of the invention is a composition where the compound having anti-HCV activity is a cyclosporin. Another aspect of the invention is where the cyclosporin is cyclosporin A.

Another aspect of the invention is a composition where the compound having anti-HCV activity is selected from the group consisting of interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

Another aspect of the invention is a composition where the compound having anti-HCV activity is effective to inhibit the function of a target selected from HCV metalloprotease, HCV serine protease, HCV polymerase, HCV helicase, HCV NS4B protein, HCV entry, HCV assembly, HCV egress, HCV NS5A protein, IMPDH, and a nucleoside analog for the treatment of an HCV infection.

Another aspect of the invention is a composition comprising a compound, or a pharmaceutically acceptable salt thereof, a pharmaceutically acceptable carrier, an interferon and ribavirin.

Another aspect of the invention is a method of inhibiting the function of the HCV replicon comprising contacting the HCV replicon with a compound or a pharmaceutically acceptable salt thereof.

Another aspect of the invention is a method of inhibiting the function of the HCV NS5B protein comprising contacting the HCV NS5B protein with a compound or a pharmaceutically acceptable salt thereof.

Another aspect of the invention is a method of treating an HCV infection in a patient comprising administering to the patient a therapeutically effective amount of a compound or a pharmaceutically acceptable salt thereof. In another embodiment the compound is effective to inhibit the function of the HCV replicon. In another embodiment the compound is effective to inhibit the function of the HCV NS5B protein.

Another aspect of the invention is a method of treating an HCV infection in a patient comprising administering to the patient a therapeutically effective amount of a compound, or a pharmaceutically acceptable salt thereof, in conjunction with (prior to, after, or concurrently) another compound having anti-HCV activity.

Another aspect of the invention is the method where the other compound having anti-HCV activity is an interferon or a ribavirin.

Another aspect of the invention is the method where the interferon is selected from interferon alpha 2B, pegylated interferon alpha, consensus interferon, interferon alpha 2A, interferon lambda, and lymphoblastoid interferon tau.

Another aspect of the invention is the method where the other compound having anti-HCV activity is a cyclosporin.

Another aspect of the invention is the method where the cyclosporin is cyclosporin A.

Another aspect of the invention is the method where the other compound having anti-HCV activity is selected from interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

Another aspect of the invention is the method where the other compound having anti-HCV activity is effective to inhibit the function of a target selected from the group consisting of HCV metalloprotease, HCV serine protease, HCV polymerase, HCV helicase, HCV NS4B protein, HCV entry, HCV assembly, HCV egress, HCV NS5A protein, IMPDH, and a nucleoside analog for the treatment of an HCV infection.

Another aspect of the invention is the method where the other compound having anti-HCV activity is effective to inhibit the function of target in the HCV life cycle other than the HCV NS5B protein.

"Therapeutically effective" means the amount of agent required to provide a meaningful patient benefit as understood by practitioners in the field of hepatitis and HCV infection.

"Patient" means a person infected with the HCV virus and suitable for therapy as understood by practitioners in the field of hepatitis and HCV infection.

"Treatment," "therapy," "regimen," "HCV infection," and related terms are used as understood by practitioners in the field of hepatitis and HCV infection.

The compounds of this invention are generally given as pharmaceutical compositions comprised of a therapeutically effective amount of a compound or its pharmaceutically acceptable salt and a pharmaceutically acceptable carrier and may contain conventional excipients. Pharmaceutically acceptable carriers are those conventionally known carriers having acceptable safety profiles. Compositions encompass all common solid and liquid forms including for example capsules, tablets, lozenges, and powders as well as liquid suspensions, syrups, elixers, and solutions. Compositions are made using common formulation techniques, and conventional excipients (such as binding and wetting agents) and vehicles (such as water and alcohols) are generally used for compositions. See, for example, *Remington's Pharmaceutical Sciences*, Mack Publishing Company, Easton, Pa., 17th edition, 1985.

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other agents will be present in a unit range similar to agents of that class used clinically. Typically, this is 0.25-1000 mg/unit.

Liquid compositions are usually in dosage unit ranges. Generally, the liquid composition will be in a unit dosage range of 1-100 mg/mL. Some examples of dosages are 1 mg/mL, 10 mg/mL, 25 mg/mL, 50 mg/mL, and 100 mg/mL. Generally, other agents will be present in a unit range similar to agents of that class used clinically. Typically, this is 1-100 mg/mL.

The invention encompasses all conventional modes of administration; oral and parenteral methods are preferred. Generally, the dosing regimen will be similar to other agents used clinically. Typically, the daily dose will be 1-100 mg/kg body weight daily. Generally, more compound is required orally and less parenterally. The specific dosing regime, however, will be determined by a physician using sound medical judgement.

The invention also encompasses methods where the compound is given in combination therapy. That is, the compound can be used in conjunction with, but separately from, other agents useful in treating hepatitis and HCV infection. In these combination methods, the compound will generally be given in a daily dose of 1-100 mg/kg body weight daily in conjunction with other agents. The other agents generally will be given in the amounts used therapeutically. The specific dosing regime, however, will be determined by a physician using sound medical judgement.

Some examples of compounds suitable for compositions and methods are listed in Table 2.

TABLE 2

| Brand Name | Physiological Class | Type of Inhibitor or Target | Source Company |
|---|---|---|---|
| NIM811 | | Cyclophilin Inhibitor | Novartis |
| Zadaxin | | Immuno-modulator | Sciclone |
| Suvus | | Methylene blue | Bioenvision |
| Actilon (CPG10101) | | TLR9 agonist | Coley |
| Batabulin (T67) | Anticancer | β-tubulin inhibitor | Tularik Inc., South San Francisco, CA |
| ISIS 14803 | Antiviral | antisense | ISIS Pharmaceuticals Inc, Carlsbad, CA/Elan Phamaceuticals Inc., New York, NY |
| Summetrel | Antiviral | antiviral | Endo Pharmaceuticals Holdings Inc., Chadds Ford, PA |
| GS-9132 (ACH-806) | Antiviral | HCV Inhibitor | Achillion/Gilead |
| Pyrazolopyrimidine compounds and salts | Antiviral | HCV Inhibitors | Arrow Therapeutics Ltd. |

TABLE 2-continued

| Brand Name | Physiological Class | Type of Inhibitor or Target | Source Company |
|---|---|---|---|
| From WO-2005047288 26 May 2005 | | | |
| Levovirin | Antiviral | IMPDH inhibitor | Ribapharm Inc., Costa Mesa, CA |
| Merimepodib (VX-497) | Antiviral | IMPDH inhibitor | Vertex Pharmaceuticals Inc., Cambridge, MA |
| XTL-6865 (XTL-002) | Antiviral | monoclonal antibody | XTL Biopharmaceuticals Ltd., Rehovot, Isreal |
| Telaprevir (VX-950, LY-570310) | Antiviral | NS3 serine protease inhibitor | Vertex Pharmaceuticals Inc., Cambridge, MA/Eli Lilly and Co. Inc., Indianapolis, IN |
| HCV-796 | Antiviral | NS5B Replicase Inhibitor | Wyeth/Viropharma |
| NM-283 | Antiviral | NS5B Replicase Inhibitor | Idenix/Novartis |
| GL-59728 | Antiviral | NS5B Replicase Inhibitor | Gene Labs/ Novartis |
| GL-60667 | Antiviral | NS5B Replicase Inhibitor | Gene Labs/ Novartis |
| 2'C MeA | Antiviral | NS5B Replicase Inhibitor | Gilead |
| PSI 6130 | Antiviral | NS5B Replicase Inhibitor | Roche |
| R1626 | Antiviral | NS5B Replicase Inhibitor | Roche |
| 2'C Methyl adenosine | Antiviral | NS5B Replicase Inhibitor | Merck |
| JTK-003 | Antiviral | RdRp inhibitor | Japan Tobacco Inc., Tokyo, Japan |
| Levovirin | Antiviral | ribavirin | ICN Pharmaceuticals, Costa Mesa, CA |
| Ribavirin | Antiviral | ribavirin | Schering-Plough Corporation, Kenilworth, NJ |
| Viramidine | Antiviral | Ribavirin Prodrug | Ribapharm Inc., Costa Mesa, CA |
| Heptazyme | Antiviral | ribozyme | Ribozyme Pharmaceuticals Inc., Boulder, CO |
| BILN-2061 | Antiviral | serine protease inhibitor | Boehringer Ingelheim Pharma KG, Ingelheim, Germany |
| SCH 503034 | Antiviral | serine protease inhibitor | Schering Plough |
| Zadazim | Immune modulator | Immune modulator | SciClone Pharmaceuticals Inc., San Mateo, CA |
| Ceplene | Immunomodulator | immune modulator | Maxim Pharmaceuticals Inc., San Diego, CA |
| CellCept | Immunosuppressant | HCV IgG immuno-suppressant | F. Hoffmann-La Roche LTD, Basel, Switzerland |
| Civacir | Immunosuppressant | HCV IgG immuno-suppressant | Nabi Biopharmaceuticals Inc., Boca Raton, FL |
| Albuferon-α | Interferon | albumin IFN-α2b | Human Genome Sciences Inc., Rockville, MD |
| Infergen A | Interferon | IFN alfacon-1 | InterMune Pharmaceuticals Inc., Brisbane, CA |
| Omega IFN | Interferon | IFN-ω | Intarcia Therapeutics |
| IFN-β and EMZ701 | Interferon | IFN-β and EMZ701 | Transition Therapeutics Inc., Ontario, Canada |
| Rebif | Interferon | IFN-β1a | Serono, Geneva, Switzerland |

TABLE 2-continued

| Brand Name | Physiological Class | Type of Inhibitor or Target | Source Company |
|---|---|---|---|
| Roferon A | Interferon | IFN-α2a | F. Hoffmann-La Roche LTD, Basel, Switzerland |
| Intron A | Interferon | IFN-α2b | Schering-Plough Corporation, Kenilworth, NJ |
| Intron A and Zadaxin | Interferon | IFN-α2b/α1-thymosin | RegeneRx Biopharma. Inc., Bethesda, MD/ SciClone Pharmaceuticals Inc, San Mateo, CA |
| Rebetron | Interferon | IFN-α2b/ribavirin | Schering-Plough Corporation, Kenilworth, NJ |
| Actimmune | Interferon | INF-γ | InterMune Inc., Brisbane, CA |
| Interferon-β | Interferon | Interferon-β-1a | Serono |
| Multiferon | Interferon | Long lasting IFN | Viragen/ Valentis |
| Wellferon | Interferon | Lympho-blastoid IFN-αn1 | GlaxoSmithKline plc, Uxbridge, UK |
| Omniferon | Interferon | natural IFN-α | Viragen Inc., Plantation, FL |
| Pegasys | Interferon | PEGylated IFN-α2a | F. Hoffmann-La Roche LTD, Basel, Switzerland |
| Pegasys and Ceplene | Interferon | PEGylated IFN-α2a/ immune modulator | Maxim Pharmaceuticals Inc., San Diego, CA |
| Pegasys and Ribavirin | Interferon | PEGylated IFN-α2a/ribavirin | F. Hoffmann-La Roche LTD, Basel, Switzerland |
| PEG-Intron | Interferon | PEGylated IFN-α2b | Schering-Plough Corporation, Kenilworth, NJ |
| PEG-Intron/ Ribavirin | Interferon | PEGylated IFN-α2b/ribavirin | Schering-Plough Corporation, Kenilworth, NJ |
| IP-501 | Liver protection | antifibrotic | Indevus Pharmaceuticals Inc., Lexington, MA |
| IDN-6556 | Liver protection | caspase inhibitor | Idun Pharmaceuticals Inc., San Diego, CA |
| ITMN-191 (R-7227) | Antiviral | serine protease inhibitor | InterMune Pharmaceuticals Inc., Brisbane, CA |
| GL-59728 | Antiviral | NS5B Replicase Inhibitor | Genelabs |
| ANA-971 | Antiviral | TLR-7 agonist | Anadys |
| Boceprevir | Antiviral | serine protease inhibitor | Schering Plough |
| TMS-435 | Antiviral | serine protease inhibitor | Tibotec BVBA, Mechelen, Belgium |
| BI-201335 | Antiviral | serine protease inhibitor | Boehringer Ingelheim Pharma KG, Ingelheim, Germany |
| MK-7009 | Antiviral | serine protease inhibitor | Merck |
| PF-00868554 | Antiviral | replicase inhibitor | Pfizer |
| ANA598 | Antiviral | Non-Nucleoside NS5B Polymerase Inhibitor | Anadys Pharmaceuticals, Inc., San Diego, CA, USA |
| IDX375 | Antiviral | Non-Nucleoside Replicase Inhibitor | Idenix Pharmaceuticals, Cambridge, MA, USA |
| BILB 1941 | Antiviral | NS5B Polymerase Inhibitor | Boehringer Ingelheim Canada Ltd R&D, Laval, QC, Canada |
| PSI-7851 | Antiviral | Nucleoside Polymerase Inhibitor | Pharmasset, Princeton, NJ, USA |

Synthetic Methods

The compounds may be made by methods known in the art including those described below. Some reagents and intermediates are known in the art. Other reagents and intermediates can be made by methods known in the art using commercially available materials. The variables (e.g. numbered "R" substituents) used to describe the synthesis of the compounds are intended only to illustrate how to make and are not to be confused with variables used in the claims or in other sections of the specification. Abbreviations used within the schemes generally follow conventions used in the art.

Abbreviations used in the schemes generally follow conventions used in the art. Chemical abbreviations used in the specification and examples are defined as follows: "NaHMDS" for sodium bis(trimethylsilyl)amide; "DMF" for N,N-dimethylformamide; "MeOH" for methanol; "NBS" for N-bromosuccinimide; "Ar" for aryl; "TFA" for trifluoroacetic acid; "LAH" for lithium aluminum hydride; "DMSO" for dimethylsulfoxide; "h" for hours; "rt" for room temperature or retention time (context will dictate); "min" for minutes; "EtOAc" for ethyl acetate; "THF" for tetrahydrofuran; "EDTA" for ethylenediaminetetraacetic acid; "Et$_2$O" for diethyl ether; "DMAP" for 4-dimethylaminopyridine; "DCE" for 1,2-dichloroethane; "ACN" for acetonitrile; "DME" for 1,2-dimethoxyethane; "HOBt" for 1-hydroxybenzotriazole hydrate; "DIEA" for diisopropylethylamine

Preparation of 2-methyl-N-(oxetan-3-ylidene)propane-2-sulfinamide

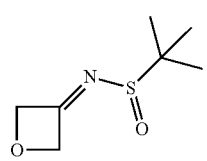

2-Methylpropane-2-sulfinamide (3.36 g, 27.77 mmol, 1 eq) and Ti(OEt)$_4$ (12 ml, 55.54 mmol, 2 eq) were added to a solution of oxetan-3-one (2 g, 27.77 mmol, 1 eq) in THF at 22° C. The reaction mixture was stirred at 50° C. for 5 h. It was cooled to room temperature and poured into saturated brine solution, and then the suspension was filtered through a pad of Cellite. The filtrate was extracted with ethyl acetate, and the organic layer washed with saturated brine solution, dried over Na$_2$SO$_4$ and concentrated. The crude product was purified by silica gel (60-120 mesh) columatography using 30% EtOAc/Petroleum ether. Yield: 0.55 g (45.4%).

$^1$H NMR (400 MHz, DMSO-d$_6$) 5.66-5.42 (m, 4H), 1.19 (s, 9H).

Preparation of 2-methyl-N-(3-(phenyloxetan-3-yl) propane-2-sulfinamide

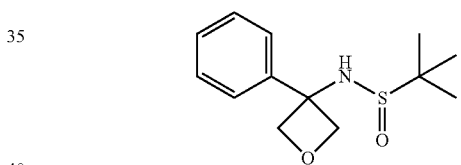

2-Bromobenzene (0.27 g, 1.71 mmol, 1.5 eq) was taken in dry THF and cooled to −78° C. A solution of n-BuLi in hexane (1.6M, 0.7 ml, 1.12 mmol, 1 eq) was then added slowly and the reaction mixture was kept at the same temperature for 60 minutes. 2-Methyl-N-(oxetan-3-ylidene)propane-2-sulfinamide (0.2 g, 1.14 mmol, 1 eq) in THF was then added slowly to the reaction mixture, and the reaction temperature maintained at −78° C. for another 1 h. The reaction mixture was then slowly warmed to 0° C., quenched with a saturated solution of NH$_4$Cl and extracted with ethyl acetate. The organic layer was separated and washed with a saturated brine solution, dried over Na$_2$SO$_4$, filtered and the filtrate concentrated. The crude product was taken for the next reaction. Yield: 0.1 g (34.6%).

LCMS: (ES+) m/z=254.2 (M+H)$^+$

Column: Symmetry Shield RP-18 (250×4.6 mm, 5 μm)

Mobile phase A: 20 mM ammonium acetate in water

Mobile phase B: MeCN

Flow: 1 ml/min

| Time | % B |
| --- | --- |
| 0.0 | 40.0 |
| 15 | 80.0 |
| 18 | 100.0 |

RetentionTime min: 1.532, wavelength: 220 nm

Preparation of 3-Phenyloxetan-3-amine

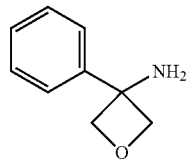 [SMILES: NC1(c2ccccc2)COC1]

2-Methyl-N-(3-(phenyloxetan-3-yl)propane-2-sulfinamide (0.1 g, 0.395 mmol, 1 eq) was taken into methanol. A solution of HCl (150 p. 1, 4N) in 1,4-dioxane was added to the reaction mixture at 0° C., which was then kept at 0° C. for 10 minutes. The reaction mixture was concentrated at low temperature and dried under vacuum to give a hydrochloride salt of the product. Yield: 25 mg (34%).

$^1$H NMR (400 MHz, CD$_3$OD) 7.57-7.47 (m, 5H), 5.15-5.13 (d, J=7.8 Hz, 2H), 4.99-4.97 (d, J=7.8 Hz, 2H).

Preparation of 2-methyl-N-(3-(pyridin-2-yl)oxetan-3-yl)propane-2-sulfinamide

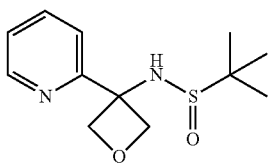 [SMILES: CC(C)(C)S(=O)NC1(c2ccccn2)COC1]

To a solution of 2-bromopyridine (0.16 g, 1.02 mmol, 1.0 eq) in dry THF at −100° C. was slowly added a solution of n-BuLi in hexane (2.5M, 0.41 ml, 1.03 mmol, 1 eq), and reaction mixture was then kept in same temperature for 30 minute. A mixture of 2-methyl-N-(oxetan-3-ylidene)propane-2-sulfinamide (0.18 g, 1.02 mmol, 1 eq) and a 2M solution of Me$_3$Al (0.5 ml, 1 mmol, 1 eq) in toluene was stirred at −78° C. for 10 minutes, and then added to the above reaction mixture slowly. The reaction temperature was maintained at −100° C. for another 1 h, after which the reaction mixture warmed to 0° C. slowly. The reaction mixture was quenched with a saturated solution of Na$_2$SO$_4$ and extracted with ethyl acetate. The organic layer was separated and washed with a saturated brine solution, dried over Na$_2$SO$_4$, filtered and the filtrate concentrated. The crude product was purified through a neutral alumina column using 0.5% MeOH/DCM. Yield: 0.1 g (38.5%).

$^1$H NMR (400 MHz, DMSO-d$_6$): 8.62 (d, J=4.4 Hz, 1H), 7.87-7.83 (m, 1H), 7.58 (d, J=8 Hz, 1H), 7.36-7.33 (m, 1H), 6.41 (s, 1H), 5.14 (d, J=6 Hz, 1H), 4.96 (d, J=6 Hz, 1H) 4.88-4.82 (m, 2H), 1.16 (s, 9H).

Column: ASCENTIS EXPRESS C18 (50×2.1 MM, 2.7 μm)
Mphase A: 10 mM ammonium formate:MeCN {98:02}
Mphase B: BUFFER:MeCN {02:98}
Flow: 1 ml/min

| Time | % A | % B |
| --- | --- | --- |
| 0.0 | 100.0 | 0 |
| 1.5 | 0.0 | 100.0 |
| 3.2 | 0.0 | 100.0 |

RT min: 1.400, wavelength: 220 nm

Preparation of 3-(pyridin-2-yl)oxetan-3-amine

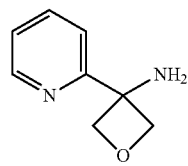 [SMILES: NC1(c2ccccn2)COC1]

2-Methyl-N-(3-(pyridin-2-yl)oxetan-3-yl)propane-2-sulfinamide (0.035 g, 0.137 mmol, 1 eq) was taken in methanol. The reaction mixture was cooled to 0° C., and was added with a solution of HCl (100 μl, 4N) in 1,4-dioxane, and then stirred at 0° C. for 10 minutes. The reaction mixture was concentrated at low temperature and dried under vacuum to give a dihydrochloride salt of the amine. Yield: 20 mg (65%). $^1$H NMR (400 MHz, DMSO-d$_6$) 9.11 (broad s, 3H), 8.68 (d, J=4.4 Hz, 1H), 8.04-8.02 (m, 1H), 7.95 (d, J=7.6 Hz 1H), 7.51 (t, J=6 Hz, 1H), 4.94-4.87 (m, 4H).

Ethyl 4-fluoro-2-(4-fluorophenyl)-5-hydroxybenzofuran-3-carboxylate

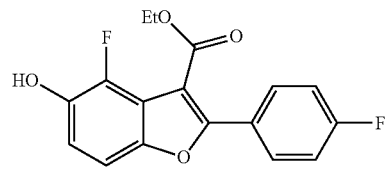 [SMILES: CCOC(=O)c1c(-c2ccc(F)cc2)oc2ccc(O)c(F)c12]

To a mixture of ethyl 2-(4-fluorophenyl)-5-hydroxybenzofuran-3-carboxylate (500 mg, 1.665 mmol) in acetonitrile (10 mL) at r.t. under N$_2$ was added 1-(chloromethyl)-4-fluoro-1,4-diazoniabicyclo[2.2.2]octane tetrafluoroborate (708 mg, 1.998 mmol). The mixture was stirred at r.t. (the mixture turned bright yellow in color) for 20 hours. The mixture was evaporated. The residue was added with 10 ml H$_2$O. The aqueous decanted, and the residue further washed with 2×5 ml H$_2$O. The mixture was dissolved in MeOH (about 10 ml), and the insoluble filtered. The filtrate was purified by Shimadzu-VP preparative reverse phase HPLC using the separation method: Solvent A=10% MeOH—90% H$_2$O—0.1% TFA, Solvent B=90% MeOH—10% H$_2$O—0.1% TFA, Start % B=60, Final % B=100, Gradient time=10 min, Stop time=12 min, Flow Rate=25 mL/min, Column: Waters-Sunfire 19×100 mm S5, Fraction Collection: 6.44-7.24 min. (UV detection at 220 nm). The desired fractions were combined and evaporated to give a yellow solid. The yellow solid was further purified by Biotage Horizon flash chromatography (0 to 70% EtOAc/Hexane, 3×80 g silica gel column) to give a light yellow solid (108.9 mg). $^1$H NMR (500 MHz, CD$_3$OD) δ 7.95 (m, 2H), 7.26 (t overlapping with dd, 2H), 7.25 (dd, 1H), 7.03 (t, J=8.39, 1H), 4.39 (q, J=7.17, 2H), 1.36 (t, J=7.17, 3H). $^{19}$F NMR (470.45 MHz, CD$_3$OD) δ −112.36, −142.29 (The $^{19}$F chemical shift was referenced to CFCl$_3$ at 0.0 ppm). The position of the F atom at C4 was confirmed by $^1$H-$^1$H through bond correlation between H6 and H7, $^1$H-$^{13}$C HMBC and F—C4 coupling in $^{13}$C NMR (125.75 MHz, CD$_3$OD) (δ 144.8 ppm, d, J=247, C4). LC/MS were performed by using Shimadzu-VP instrument with UV detection at 220 nm and Waters Micromass. HPLC method: Solvent A=10% MeOH—90% H$_2$O—0.1% TFA, Solvent B=90% MeOH—10% H$_2$O—0.1% TFA, Start % B=0, Final % B=100, Gradient time=2 min, Stop time=3 min, Flow Rate=5 ml/min, Column: Phenomenex-Luna, 3.0×50 mm, S10; (ES+) m/z (M+H)$^+$=319.14, HPLC R$_t$=1.718 min. The minor fractions collected at about 7.69-8.20 min. was confirmed by $^1$H-$^1$H through bond correlation, $^1$H-$^{13}$C HMBC and F—C6 coupling in $^{13}$C NMR (125.75 MHz, CD$_3$OD) (δ 152.5 ppm, d, J=242 Hz, C6) to be the isomer of the F-atom at C6 (C4: C6 about 3:1 based on preparative HPLC % area of the UV trace); $^1$H NMR (500 MHz, CD$_3$OD) δ 8.04 (dd, J=8.55, 5.49, 2H), 7.59 (d, J=8.85, 1H), 7.38 (d, J=10.07, 1H), 7.25 (t, J=8.70, 2H), 4.40 (q, J=7.17, 2H), 1.41 (t, J=7.17, 3H). $^{19}$F NMR (470.45 MHz, CD$_3$OD) δ −112.29, −138.52. LC/MS were performed by using Shimadzu-VP instrument with UV detection at 220 nm and Waters Micromass. HPLC method: Solvent A=10% MeOH—90% H$_2$O—0.1% TFA, Solvent B=90% MeOH—10% H$_2$O—0.1% TFA, Start % B=0, Final % B=100, Gradient time=2 min, Stop time=3 min, Flow Rate=5 ml/min, Column: Phenomenex-Luna, 3.0×50 mm, S10; (ES+) m/z (M+H)$^+$=319.14, HPLC R$_t$=1.798 min. (Alternatively, the two isomers were separated after the ester hydrolysis by Shimadzu-VP preparative reverse phase HPLC using the same method as above but with Start % B=40).

4-Fluoro-2-(4-fluorophenyl)-5-hydroxybenzofuran-3-carboxylic acid

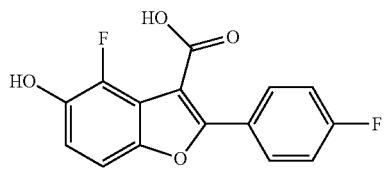 [SMILES: O=C(O)c1c(-c2ccc(F)cc2)oc2ccc(O)c(F)c12]

To a mixture of ethyl 4-fluoro-2-(4-fluorophenyl)-5-hydroxybenzofuran-3-carboxylate (108.9 mg, 0.342 mmol) in a mixture of MeOH (2 mL)/THF (2 mL) at r.t. under N$_2$ was added sodium hydroxide (1.0 mL, 1.0 mmol) (1 M aq.). The mixture was stirred at 100° C. for 1.5 hours. The mixture was cooled to r.t., added with 1.5 ml 1N HCl, and then added 10 ml H$_2$O. The white precipitates were filtered and washed with 3×2 ml H$_2$O and dried (73 mg). $^1$H NMR (500 MHz, CD$_3$OD) δ 7.98 (m, 2H), 7.25 (t overlapping with dd, 2H), 7.24 (dd, 1H), 7.02 (t, J=8.39, 1H). LC/MS were performed by using Shimadzu-VP instrument with UV detection at 220 nm and Waters Micromass. HPLC method: Solvent A=10% MeOH—90% H$_2$O—0.1% TFA, Solvent B=90% MeOH—10% H$_2$O—0.1% TFA, Start % B=0, Final % B=100, Gradient time=2 min, Stop time=3 min, Flow Rate=5 ml/min, Column: Phenomenex-Luna, 3.0×50 mm, S10; (ES+) m/z (M+H)$^+$=291.01, HPLC R$_t$=1.478 min.

4-Fluoro-2-(4-fluorophenyl)-5-hydroxy-N-methyl-benzofuran-3-carboxamide

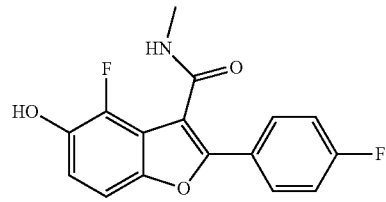 [SMILES: CNC(=O)c1c(-c2ccc(F)cc2)oc2ccc(O)c(F)c12]

To a mixture of 4-fluoro-2-(4-fluorophenyl)-5-hydroxybenzofuran-3-carboxylic acid (73 mg, 0.252 mmol), methylamine, HCl (25.5 mg, 0.377 mmol), HOBT hydrate (65.5 mg, 0.428 mmol) and EDC hydrochloride (87 mg, 0.453 mmol) at r.t. under N$_2$ was added N,N-diisopropylethylamine (0.220 mL, 1.258 mmol). The mixture was stirred at r.t. for 16 hours. After concentration, the mixture was added with 5 ml 1N HCl, and then 14 ml H$_2$O. The white solid was filtered and washed with 3×5 ml H$_2$O and dried (64 mg). $^1$H NMR (500 MHz, CD$_3$OD) δ 7.89 (dd, J=8.09, 5.34, 2H), 7.25 (t overlapping with dd, 2H), 7.23 (dd, 1H), 6.99 (t, J=8.55, 1H), 2.96 (s, 3H). LC/MS were performed by using Shimadzu-VP instrument with UV detection at 220 nm and Waters Micromass. HPLC method: Solvent A=10% MeOH—90% H$_2$O—0.1% TFA, Solvent B=90% MeOH—10% H$_2$O—0.1% TFA, Start % B=0, Final % B=100, Gradient time=2 min, Stop time=3 min, Flow Rate=5 ml/min, Column: Phenomenex-Luna, 3.0×50 mm, S10; (ES+) m/z (M+H)$^+$=304.06, HPLC R$_t$=1.262 min.

4-Fluoro-2-(4-fluorophenyl)-3-(methylcarbamoyl)benzofuran-5-yl trifluoromethanesulfonate

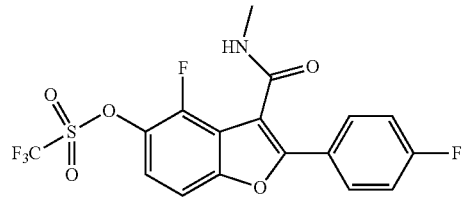 [SMILES: CNC(=O)c1c(-c2ccc(F)cc2)oc2ccc(OS(=O)(=O)C(F)(F)F)c(F)c12]

To a white suspension of 4-fluoro-2-(4-fluorophenyl)-5-hydroxy-N-methylbenzofuran-3-carboxamide (64 mg, 0.211 mmol) in CH$_2$Cl$_2$ (2 mL) at r.t. under N$_2$ was added triethylamine (0.059 mL, 0.422 mmol). The mixture was cooled to 0° C., and then added 1,1,1-trifluoro-N-phenyl-N-(trifluoromethylsulfonyl)methanesulfonamide (113 mg, 0.317 mmol). The mixture was then stirred at r.t. (the white suspension turned into a light yellow solution after stirring for about 10 min) for 2 hours 35 min. The mixture was left standing at r.t. overnight, and then evaporated. The residue was cooled in an ice-water bath, added with 2 ml H$_2$O. The solids were filtered and washed with 3×2 ml H$_2$O, and dried (94 mg). $^1$H NMR (500 MHz, CD$_3$OD) δ 7.95 (m, 2H), 7.59 (dd, J=9.00, 1.00, 1H), 7.50 (dd, J=9.00, 7.50, 1H), 7.30 (t, J=8.55, 2H), 2.99 (s, 3H). LC/MS were performed by using Shimadzu-VP instrument with UV detection at 220 nm and Waters Micromass. HPLC method: Solvent A=10% MeOH—90% H$_2$O—0.1% TFA, Solvent B=90% MeOH—10% H$_2$O—0.1% TFA, Start % B=0, Final % B=100, Gradient time=2 min, Stop time=3 min, Flow Rate=5 ml/min, Column: Phenomenex-Luna, 3.0×50 mm, S10; (ES+) m/z (M+H)$^+$=436.04, HPLC R$_t$=1.678 min.

Methyl 5-(4-fluoro-2-(4-fluorophenyl)-3-(methylcarbamoyl)benzofuran-5-yl)-2-methoxy-4-methylbenzoate

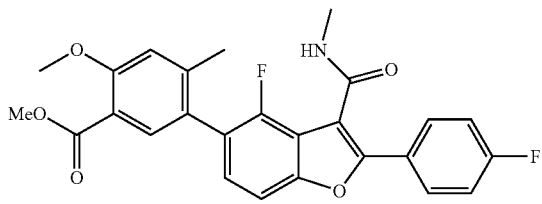 [SMILES: CNC(=O)c1c(-c2ccc(F)cc2)oc2ccc(-c3cc(C(=O)OC)c(OC)cc3C)c(F)c12]

A mixture of the above prepared 4-fluoro-2-(4-fluorophenyl)-3-(methylcarbamoyl)benzofuran-5-yl trifluoromethanesulfonate (assumed 0.211 mmol), methyl 2-methoxy-4-methyl-5-(4,4,5,5-tetramethyl-1,3,2-dioxaborolan-2-yl)benzoate (0.078 g, 0.253 mmol), (Ph$_3$P)$_4$Pd (0.024 g, 0.021 mmol) and cesium carbonate (0.103 g, 0.317 mmol) in a mixture of H$_2$O (0.2 mL)/1,4-dioxane (1 mL) was stirred at 95° C. for 2 hours 30 min. The mixture was left standing at r.t. overnight. The mixture was diluted with 3.5 ml 1,4-dioxane, filtered through a Whatman PVDF 0.45 um disk (with 3×1 ml washing). The filtrate was concentrated. The mixture was added with 3.5 ml 1N HCl, and then 6 ml H$_2$O (yellow solid deposited on the wall of the flask). The aqueous was decanted, and the residue washed with 3×2 ml H$_2$O and dried. LC/MS were performed by using Shimadzu-VP instrument with UV detection at 220 nm and Waters Micromass. HPLC method: Solvent A=10% MeOH—90% H$_2$O—0.1% TFA, Solvent B=90% MeOH—10% H$_2$O—0.1% TFA, Start % B=0, Final % B=100, Gradient time=2 min, Stop time=3 min, Flow Rate=5 ml/min, Column: Phenomenex-Luna, 3.0×50 mm, S10; (ES+) m/z (M+H)$^+$=466.27, HPLC R$_t$=1.708 min.

5-(4-Fluoro-2-(4-fluorophenyl)-3-(methylcarbamoyl)benzofuran-5-yl)-2-methoxy-4-methylbenzoic acid

To the above prepared methyl 5-(4-fluoro-2-(4-fluorophenyl)-3-(methylcarbamoyl)benzofuran-5-yl)-2-methoxy-4-methylbenzoate (assumed 0.211 mmol) in a mixture MeOH (2 mL)/THF (2 mL) at r.t. under N$_2$ was added sodium hydroxide (0.84 mL, 0.84 mmol). The mixture was stirred at r.t. for 24 hours. The mixture was added with 2 ml 1N HCl, and concentrated until off white solids formed. The mixture was added with 5 ml H$_2$O, the solids filtered and washed with 3×2 ml H$_2$O and dried (75.1 mg). $^1$H NMR (500 MHz, CD$_3$OD) δ 7.95 (m, 2H), 7.73 (s, 1H), 7.51 (d, J=8.24, 1H), 7.30-7.25 (t ovelapping with m, 3H), 7.13 (s, 1H), 3.99 (s, 3H), 2.96 (s, 3H), 2.28 (s, 3H). LC/MS were performed by using Shimadzu-VP instrument with UV detection at 220 nm and Waters Micromass. HPLC method: Solvent A=10% MeOH—90% H$_2$O—0.1% TFA, Solvent B=90% MeOH—10% H$_2$O—0.1% TFA, Start % B=0, Final % B=100, Gradient time=2 min, Stop time=3 min, Flow Rate=5 ml/min, Column: Phenomenex-Luna, 3.0×50 mm, S10; (ES+) m/z (M+H)$^+$=452.23, HPLC R$_t$=1.582.

The following intermediates were prepared in a similar manner as described.

Methyl 3-fluoro-5-(4-fluoro-2-(4-fluorophenyl)-3-(methylcarbamoyl)benzofuran-5-yl)-4-methylbenzoate

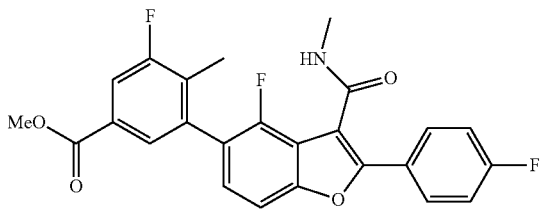

LC/MS were performed by using Shimadzu-VP instrument with UV detection at 220 nm and Waters Micromass. HPLC method: Solvent A=10% MeOH—90% H$_2$O—0.1% TFA, Solvent B=90% MeOH—10% H$_2$O—0.1% TFA, Start % B=0, Final % B=100, Gradient time=2 min, Stop time=3 min, Flow Rate=5 ml/min, Column: Phenomenex-Luna, 3.0×50 mm, S10; (ES+) m/z (M+H)$^+$=454.08, HPLC R$_t$=1.838 min.

3-Fluoro-5-(4-fluoro-2-(4-fluorophenyl)-3-(methylcarbamoyl)benzofuran-5-yl)-4-methylbenzoic acid

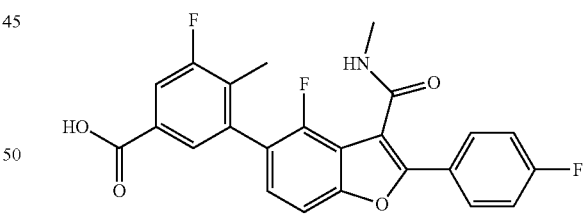

$^1$H NMR (500 MHz, CD$_3$OD) δ 7.96 (m, 2H), 7.76 (s, 1H), 7.75-7.73 (d, 1H), 7.56 (d, J=8.24, 1H), 7.33-7.28 (t ovelapping with m, 3H), 2.96 (s, 3H), 2.20 (s, 3H). LC/MS were performed by using Shimadzu-VP instrument with UV detection at 220 nm and Waters Micromass. HPLC method: Solvent A=10% MeOH—90% H$_2$O—0.1% TFA, Solvent B=90% MeOH—10% H$_2$O—0.1% TFA, Start % B=0, Final % B=100, Gradient time=2 min, Stop time=3 min, Flow Rate=5 ml/min, Column: Phenomenex-Luna, 3.0×50 mm, S10; (ES+) m/z (M+H)$^+$=440.09, HPLC R$_t$=1.720.

The following acid intermediate was prepared by either one of the methods shown below in a similar manner as described.

3-(4-Fluoro-2-(4-fluorophenyl)-3-(methylcarbamoyl)benzofuran-5-yl)-4-methylbenzoic acid
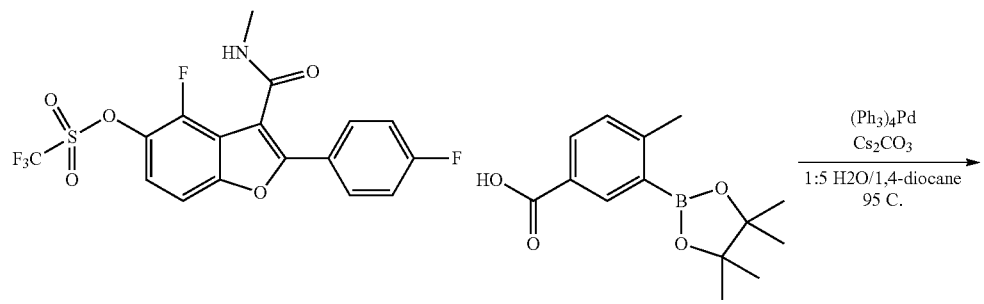
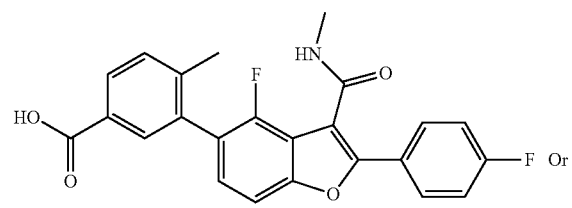
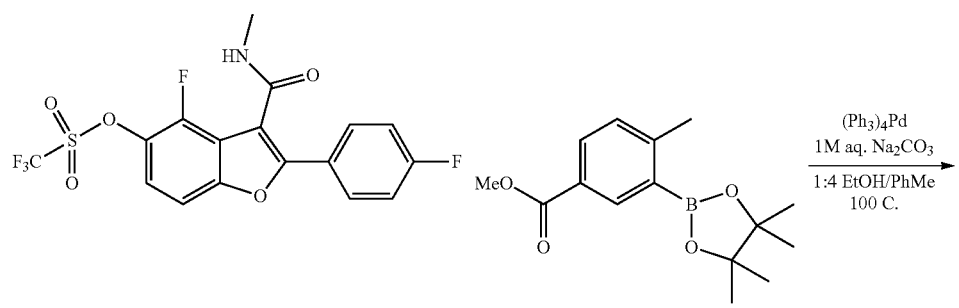
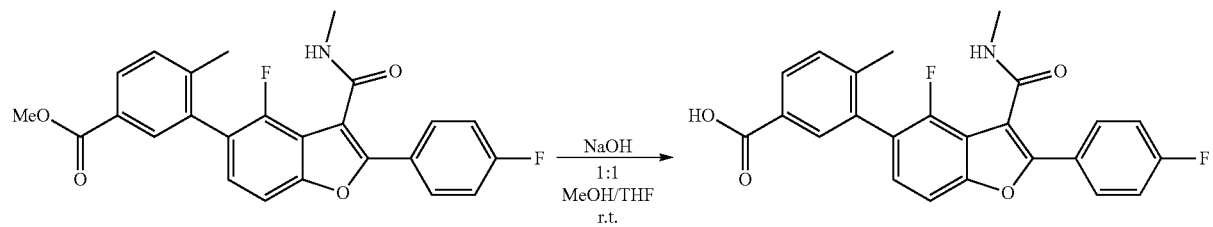
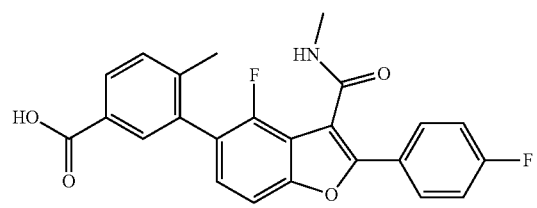 [SMILES: CNC(=O)c1c(-c2ccc(F)cc2)oc2ccc(-c3cc(C(=O)O)c(OC)cc3C)c(F)c12]

LC/MS were performed by using Shimadzu-VP instrument with UV detection at 220 nm and Waters Micromass. HPLC method: Solvent A=10% MeOH—90% H$_2$O—0.1% TFA, Solvent B=90% MeOH—10% H$_2$O—0.1% TFA, Start % B=0, Final % B=100, Gradient time=2 min, Stop time=3 min, Flow Rate=5 ml/min, Column: Phenomenex-Luna, 3.0×50 mm, S10; (ES+) m/z (M+H)$^+$=422.19, HPLC R$_t$=1.653 min.

Synthesis of 4-fluoro-2-(4-fluorophenyl)-N-methyl-5-(2-methyl-5-(3-(phenyloxetan-3-ylcarbamoyl)phenyl)benzofuran-3-carboxamide

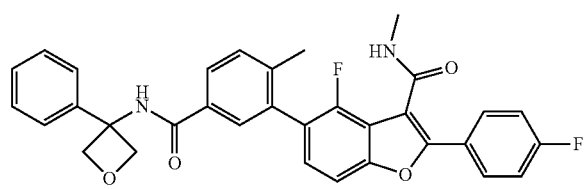 [SMILES: CNC(=O)c1c(-c2ccc(F)cc2)oc2ccc(-c3cc(C(=O)NC4(c5ccccc5)COC4)ccc3C)c(F)c12]

To a mixture of 3-(4-fluoro-2-(4-fluorophenyl)-3-(methylcarbamoyl)benzofuran-5-yl)-4-methylbenzoic acid (30 mg, 0.07 mmol, 1.0 eq) and 3-phenyloxetan-3-amine HCl (25 mg, 0.135 mmol, 1.9 eq) in 1.0 ml DMF at 0° C. was added TEA (48 µl, 0.35 mmol, 5.0 eq) and (benzotriazol-1-yloxy)tris(dimethylamino)phosphonium hexafluorophosphate (BOP reagent) (37 mg, 0.08 mmol, 1.2 eq). The reaction mixture was stirred as rt overnight. The reaction mixture was diluted with water and extracted with EtOAc. The organic layer was washed with brine, dried over Na$_2$SO$_4$, filtered and the filtrate concentrated. The crude product was purified by preparative TLC using acetone/n-hexane (30:70) as a mobile phase. Yield: 7.0 mg (18%).

$^1$H NMR (400 MHz, CDCl$_3$): δ 7.99-7.96 (m, 2H), 7.80 (dd, J=2, 8 Hz, 1H), 7.74 (d, J=2 Hz, 1H), 7.58-7.56 (m, 2H), 7.42-7.37 (m, 5H), 7.32-7.30 (m, 1H), 7.21-7.15 (m, 3H), 6.86 (broad s, 1H), 5.14 (d, J=6.8 Hz, 2H), 5.03 (d, J=6.8 Hz, 2H), 3.02 (d, J=4.8 Hz, 3H), 2.28 (s, 3H).

$^{19}$F NMR (376.57 MHz, CDCl$_3$) δ −109.64, −119.32 (The $^{19}$F chemical shift was referenced to CFCl$_3$ at 0.0 ppm).

LCMS: (ES+) m/z=553.2 (M+H)$^+$

Column-Xbridge phe (4.6×30 mm-3.5 µm)

Mphase A: 2% MeCN—98% H$_2$O—10 mM NH$_4$COOH

Mphase B: 98% MeCN—2% H$_2$O—10 mM NH$_4$COOH

Flow: 1 ml/min

| Time | % A | % B |
| --- | --- | --- |
| 0.0 | 100.0 | 0 |
| 1.5 | 0.0 | 100.0 |
| 3.2 | 0.0 | 100.0 |

RT min: 1.748, wavelength: 220 nm

HPLC Method: SUNFIRE C18 (4.6×150) mm, 3.5 micron

Buffer: 0.05% TFA in water pH 2.5

Mobile Phase A: Buffer:MeCN (95:5)

Mobile Phase B: MeCN:Buffer (95:5)

Flow: 1 ml/min

| Time | B % |
| --- | --- |
| 0 | 10 |
| 12 | 100 |
| 15 | 100 |

Wavelength: 254 nm, RT min: 11.522
Wavelength: 220 nm, RT min: 11.522
HPLC Method: XBridege phenyl (4.6×150) mm, 3.5 micron
Buffer: 0.05% TFA in water pH 2.5
Mobile Phase A: 0.05% TFA in water:MeCN (95:5)
Mobile Phase B: MeCN: 0.05% TFA in water (95:5)
Flow: 1 ml/min

| Time | B % |
| --- | --- |
| 0 | 10 |
| 12 | 100 |
| 15 | 100 |

Wavelength: 254 nm, RT Min: 10.736
Wavelength: 220 nm, RT min: 10.736

Synthesis of 4-fluoro-2-(4-fluorophenyl)-N-methyl-5-(2-methyl-5-(3-(pyridin-2-yl)oxetan-3-ylcarbamoyl)phenyl)benzofuran-3-carboxamide

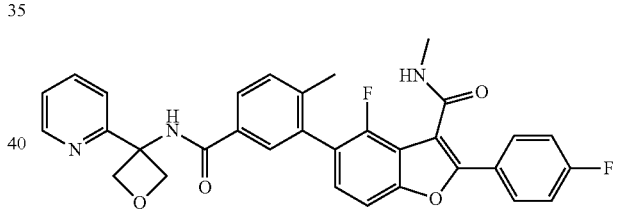

To a mixture of 3-(4-fluoro-2-(4-fluorophenyl)-3-(methylcarbamoyl)benzofuran-5-yl)-4-methylbenzoic acid (0.045 g, 0.107 mmol, 1.0 eq) and 3-(pyridin-2-yl)oxetan-3-amine.2HCl (0.025 g, 0.112 mmol, 1.05 eq) in DMF at 0° C. was added TEA (0.15 ml, 1.08 mmol, 10 eq) and BOP reagent (0.06 g, 0.136 mmol, 1.3 eq). The reaction mixture was stirred as rt overnight. The reaction mixture was diluted with water and extracted with EtOAc. The organic layer was washed with brine, dried over Na$_2$SO$_4$, filtered and the filtrate concentrated. The crude product was purified by preparative HPLC. Yield: 0.015 g (25.4%).

$^1$H NMR (400 MHz, CD$_3$OD): δ 8.67-8.65 (m, 1H), 7.97-7.91 (m, 3H), 7.86 (d, J=2 Hz, 1H), 7.81 (dt, J=2, 7.8 Hz, 1H), 7.56-7.52 (m, 2H), 7.50 (d, J=8.4 Hz, 1H), 7.35-7.29 (m, 4H), 5.15 (d, J=6.8 Hz, 2H), 5.09 (d, J=6.8 Hz, 2H), 2.95 (s, 3H), 2.30 (s, 3H).

$^{19}$F NMR (376.57 MHz, DMSO-d$_6$) δ −113.06, −123.51.

LCMS: (ES+) m/z=554.0 (M+H)$^+$

Column-Xbridge phe (4.6×30 mm-3.5 µm)

Mphase A: 2% MeCN—98% H$_2$O—10 mM NH$_4$COOH

Mphase B: 98% MeCN—2% H$_2$O—10 mM NH$_4$COOH

Flow: 1 ml/min

| Time | % A | % B |
|---|---|---|
| 0.0 | 100.0 | 0 |
| 1.5 | 0.0 | 100.0 |
| 3.2 | 0.0 | 100.0 |

RT min: 1.649, wavelength: 220 nm
HPLC Method: SUNFIRE C18 (4.6×150) mm, 3.5 micron
Buffer: 0.05% TFA in water pH 2.5
Mobile Phase A: Buffer:MeCN (95:5)
Mobile Phase B: MeCN:Buffer (95:5)
Flow: 1 ml/min

| Time | B % |
|---|---|
| 0 | 10 |
| 12 | 100 |
| 15 | 100 |

Wavelength: 254 nm, RT min: 9.567
Wavelength: 220 nm, RT min: 9.567
HPLC Method: XBridege phenyl (4.6×150) mm, 3.5 micron
Buffer: 0.05% TFA in water pH 2.5
Mobile Phase A: 0.05% TFA in water:MeCN (95:5)
Mobile Phase B: MeCN: 0.05% TFA in water (95:5)
Flow: 1 ml/min

| Time | B % |
|---|---|
| 0 | 10 |
| 12 | 100 |
| 15 | 100 |

Wavelength: 254 nm, RT Min: 9.309
Wavelength: 220 nm, RT min: 9.309
Preparative HPLC Method
Column: CHROMASILC4 (4.6×150) mm, 5 micron
Mobile Phase A: 20 mM AMMONIUM ACETATE in Water
Mobile Phase B: MeCN
FLOW: 1 ml/min,

| Time | B % |
|---|---|
| 0 | 40 |
| 18 | 80 |

| Time | B % |
|---|---|
| 20 | 100 |
| 26 | 100 |

RT: 11.647 min

Synthesis of 4-fluoro-2-(4-fluorophenyl)-5-(4-methoxy-2-methyl-5-(3-pyridin-2-yl)oxetan-3-ylcarbamoyl)phenyl)-N-methylbenzofuran-3-carboxamide

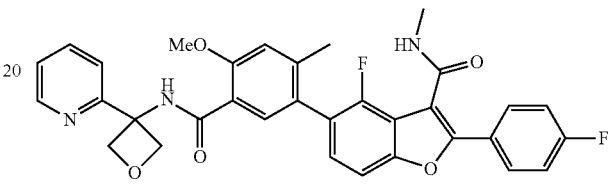

To a mixture of 5-(4-fluoro-2-(4-fluorophenyl)-3-(methylcarbamoyl)benzofuran-5-yl)-2-methoxy-4-methylbenzoic acid (0.040 g, 0.089 mmol, 1.0 eq) and 3-(pyridin-2-yl)oxetan-3-amine 2HCl (0.028 g, 0.126 mmol, 1.4 eq) in DMF at 0° C. was added TEA (0.15 ml, 1.08 mmol, 12 eq) and BOP reagent (0.06 g, 0.136 mmol, 1.5 eq). The reaction mixture was stirred as rt overnight. The reaction mixture was diluted with water and extracted with EtOAc. The organic layer was washed with brine, dried over $Na_2SO_4$, filtered and the filtrate concentrated. The crude product was purified by SFC. Yield: 0.010 g (19.6%).

$^1$H NMR (400 MHz, $CDCl_3$): δ 9.26 (s, 1H), 8.67-7.66 (m, 1H), 8.08 (s, 1H), 8.01-7.97 (m, 2H), 7.75-7.73 (m, 2H), 7.38 (d, J=8.8 Hz, 1H), 7.22-7.15 (m, 4H), 6.97 (s, 1H), 6.17 (broad s, 1H), 5.32 (d, J=6.4 Hz, 2H), 5.11 (d, J=6.4 Hz, 2H), 4.11 (s, 3H), 3.02 (d, J=4.8 Hz, 3H), 2.28 (s, 3H).

$^{19}$F NMR (376.57 MHz, $CDCl_3$) δ −109.93, −119.28.

LCMS: (ES+) m/z=584.0 $(M+H)^+$
Column-Xbridge phe (4.6×30 mm-3.5 nm)
Mphase A: 2% MeCN—98% $H_2O$—10 mM $NH_4COOH$
Mphase B: 98% MeCN—2% $H_2O$—10 mM $NH_4COOH$
Flow: 1 ml/min

| Time | % A | % B |
|---|---|---|
| 0.0 | 100.0 | 0 |
| 1.5 | 0.0 | 100.0 |
| 3.2 | 0.0 | 100.0 |

RT min: 1.692, wavelength: 220 nm
HPLC Method: SUNFIRE C18 (4.6×150) mm, 3.5 micron
Buffer: 0.05% TFA in water pH 2.5
Mobile Phase A: Buffer:MeCN (95:5)
Mobile Phase B: MeCN:Buffer (95:5)
Flow: 1 ml/min

| Time | B % |
|---|---|
| 0 | 10 |
| 12 | 100 |
| 15 | 100 |

Wavelength: 254 nm, RT min: 9.834
Wavelength: 220 nm, RT min: 9.834
HPLC Method: XBridege phenyl (4.6×150) mm, 3.5 micron
Buffer: 0.05% TFA in water pH 2.5
Mobile Phase A: 0.05% TFA in water:MeCN (95:5)
Mobile Phase B: MeCN: 0.05% TFA in water (95:5)
Flow: 1 ml/min

| Time | B % |
|---|---|
| 0 | 10 |
| 12 | 100 |
| 15 | 100 |

Wavelength: 254 nm, RT Min: 9.623
Wavelength: 220 nm, RT min: 9.623
SFC Method
Column: Chiral Pack IC (250×4.6)mm, 5 micron
Co-solvent: Methanol
$CO_2$ flow rate: 1.75 ml/min
Co-solvent flow rate: 1.75 ml/min
Co-solvent %: 50
Total flow: 3.5 ml/min
Front pressure: 225
Back pressure: 152
Pressure drop: 73

Synthesis of 4-fluoro-5-(3-fluoro-2-methyl-5-(3-(pyridin-2-yl)oxetan-3-ylcarbamoyl)phenyl)-2-(4-fluorophenyl)-N-methylbenzofuran-3-carboxamide

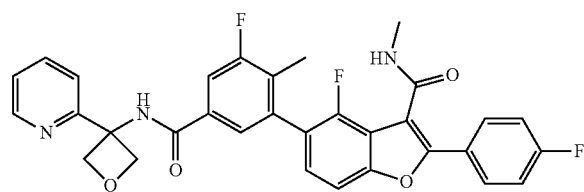 [SMILES: CNC(=O)c1c(-c2ccc(F)cc2)oc2ccc(-c3cc(C(=O)NC4(c5ccccn5)COC4)cc(F)c3C)c(F)c12]

To a mixture of 3-fluoro-5-(4-fluoro-2-(4-fluorophenyl)-3-(methylcarbamoyl)benzofuran-5-yl)-4-methylbenzoic acid (0.050 g, 0.114 mmol, 1.0 eq) and 3-(pyridin-2-yl)oxetan-3-amine 2HCl (0.03 g, 0.134 mmol, 1.2 eq) in DMF at 0° C. was added TEA (0.15 ml, 1.08 mmol, 9 eq) and BOP reagent (0.06 g, 0.136 mmol, 1.2 eq). The reaction mixture was stirred as rt overnight. The reaction mixture was diluted with water and extracted with EtOAc. The organic layer was washed with brine, dried over $Na_2SO_4$ filtered and the filtrate concentrated. The crude product was purified by preparative HPLC. Yield: 0.010 g (15.3%).

$^1$H NMR (400 MHz, $CD_3OD$): δ 8.67-8.65 (m, 1H), 7.98-7.94 (m, 2H), 7.83 (dt, J=1.6, 7.8 Hz, 1H), 7.75-7.72 (m, 2H), 7.59-7.54 (m, 2H), 7.38-7.34 (m, 2H), 7.33-7.28 (m, 2H), 5.15 (d, J=6.8 Hz, 2H), 5.10 (d, J=6.8 Hz, 2H), 2.96 (s, 3H), 2.22 (s, 3H).

$^{19}$F NMR (376.57 MHz, $CD_3OD$) δ −112.13, −116.31, −122.57.
LCMS: (ES+) m/z=572.0 $(M+H)^+$
Column-Xbridge phe (4.6×30 mm-3.5 μm)
Mphase A: 2% MeCN—98% $H_2O$—10 mM $NH_4COOH$
Mphase B: 98% MeCN—2% $H_2O$—10 mM $NH_4COOH$
Flow: 1 ml/min

| Time | % A | % B |
|---|---|---|
| 0.0 | 100.0 | 0 |
| 1.5 | 0.0 | 100.0 |
| 3.2 | 0.0 | 100.0 |

RT min: 1.701, wavelength: 220 nm
HPLC Method: SUNFIRE C18 (4.6×150) mm, 3.5 micron SC/862
Buffer: 0.05% TFA in water pH 2.5
Mobile Phase A: Buffer:MeCN (95:5)
Mobile Phase B: MeCN:Buffer (95:5)
Flow: 1 ml/min

| Time | B % |
|---|---|
| 0 | 10 |
| 12 | 100 |
| 15 | 100 |

Wavelength: 254 nm, RT min: 9.871
Wavelength: 220 nm, RT min: 9.871
HPLC Method: X Bridge phenyl (4.6×150) mm, 3.5 micron
Buffer: 0.05% TFA in water pH 2.5
Mobile Phase A: 0.05% TFA in water:MeCN (95:5)
Mobile Phase B: MeCN: 0.05% TFA in water (95:5)
Flow: 1 ml/min

| Time | B % |
|---|---|
| 0 | 10 |
| 12 | 100 |
| 15 | 100 |

Wavelength: 254 nm, RT Min: 9.649
Wavelength: 220 nm, RT min: 9.649
Preparative HPLC Method
Column: Xbridge C18 (4.6×150) mm, 5 micron
Mobile Phase A: 20 mM AMMONIUM ACETATE in Water
Mobile Phase B: MeCN
Flow: 1 ml/min,

| Time | B % |
| --- | --- |
| 0 | 50 |
| 15 | 80 |
| 20 | 80 |
| 22 | 50 |

RT: 8.065 min

Preparation of N-(3-cyanooxetan-3-yl)-2-methylpropane-2-sulfinamide

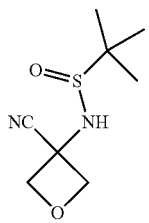

To a yellow solution of 2-methyl-N-(oxetan-3-ylidene)propane-2-sulfinamide (1 g, 5.71 mmol) in CH$_2$Cl$_2$ (20 ml) in a 100 round-bottomed flask was added titanium tetraethoxide (0.651 g, 2.85 mmol) and the reaction mixture stirred for 10 min. TMSCN (1.530 ml, 11.41 mmol) was then added, and the resulting reaction mixture stirred at r.t. for overnight. The reaction mixture was poured into saturated brine solution, and then the suspension was filtered through a pad of Celite. The organic layer was separated, and the aqueous layer extracted with ethyl acetate (3×25 ml). The combined organic solution was washed with saturated brine solution, dried over Na$_2$SO$_4$, filtered and concentrated. The crude product was purified over neutral alumina column using 4% methanol in dichloromethane as eluent. Desired fractions were collected and concentrated to give the titled product as colorless oil (0.9 g, 78%).

$^1$H NMR (400 MHz, DMSO-d$_6$): δ 6.78 (s, 1H), 4.91 (q, 2H), 4.70 (d, J=7.2 Hz, 1H), 4.64 (d, J=6.8 Hz, 1H), 1.18 (s, 9H).

LCMS: (ES+) m/z observed=202.7

Column-Ascentis Express C18 (5×2.1 mm-2.7 nm)

Mobilephase A: 2% MeCN—98% H$_2$O—10 mM NH$_4$COOH

Mobilephase B: 98% MeCN—2% H$_2$O—10 mM NH$_4$COOH

Flow: 1 ml/Min

| Time | % A | % B |
| --- | --- | --- |
| 0.0 | 100.0 | 0 |
| 1.4 | 0.0 | 100.0 |
| 3.0 | 0.0 | 100.0 |

RetentionTime (RT) min: 1.41, wavelength: 220 nm

Preparation of 3-(1,1-dimethylethylsulfinamido)oxetane-3-carboximidamide

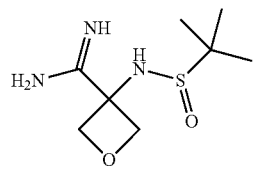

To a mixture of N-(3-cyanooxetan-3-yl)-2-methylpropane-2-sulfinamide (0.1 g, 0.494 mmol) in methanol (2 ml) in a 50 ml sealed tube was added N-acetyl-L-(+)-cysteine (0.081 g, 0.494 mmol), and the reaction mixture stirred for few minutes. A solution of ammonia in methanol (0.5 ml, 3.50 mmol, 7 N) was added, and the reaction mixture stirred at 60° C. for overnight. The reaction mixture was then concentrated under vacuum, and the crude was used for the next step without further purification.

LCMS: (ES+) m/z=220.7 (M+H)$^+$

Column-Ascentis Express C18 (5×2.1 mm-2.7 μm)

Mphase A: 2% MeCN—98% H$_2$O—10 mM NH$_4$COOH

Mphase B: 98% MeCN—2% H$_2$O—10 mM NH$_4$COOH

Flow: 1 ml/Min

| Time | % A | % B |
| --- | --- | --- |
| 0.0 | 100.0 | 0 |
| 1.4 | 0.0 | 100.0 |
| 3.0 | 0.0 | 100.0 |

RT min: 0.8, wavelength: 220 nm

Preparation of 2-methyl-N-(3-(pyrimidin-2-yl)oxetan-3-yl)propane-2-sulfinamide

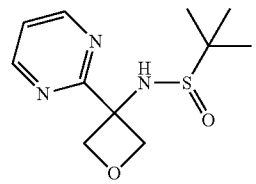 [SMILES: CC(C)(C)S(=O)NC1(c2ncccn2)COC1]

To a yellow solution of 3-(1,1-dimethylethylsulfinamido)oxetane-3-carboximidamide (crude from above, assumed 0.494 mmol) in MeOH (2 ml) in a 50 ml sealed tube was added (E)-3-(dimethylamino)acrylaldehyde (0.090 g, 0.912 mmol), and the reaction mixture stirred for 10 min. Sodium methoxide (0.43 ml, 1.824 mmol, 25 wt % in MeOH) was added to the mixture, which was then stirred at 65° C. for overnight. The reaction mixture was diluted with ethyl acetate and washed with water. The aqueous layer was back extracted with ethyl acetate (3×25 ml). The combined organic layers was washed with saturated brine solution, dried over Na$_2$SO$_4$, filtered and concentrated. The crude material was purified by pre-HPLC. Overall yield of two steps: (30 mg, 24%).

$^1$H NMR (400 MHz, DMSO-d$_6$): δ 8.88 (d, J=4.8 Hz, 2H), 7.48 (t, J=4.8 Hz, 1H), 6.32 (broad s, 1H), 5.12 (d, J=6.4 Hz, 1H), 4.99 (d, J=6.4 Hz, 1H), 4.93 (d, J=6.4 Hz, 1H), 4.84 (d, J=6.4 Hz, 1H), 1.09 (s, 9H).

LCMS: (ES+) m/z observed=255.7
Column-Ascentis Express C18 (5×2.1 mm-2.7 nm)
Mphase A: 2% MeCN—98% $H_2O$—10 mM $NH_4COOH$
Mphase B: 98% MeCN—2% $H_2O$—10 mM $NH_4COOH$
Flow: 1 ml/Min

| Time | % A | % B |
|---|---|---|
| 0.0 | 100.0 | 0 |
| 1.4 | 0.0 | 100.0 |
| 3.0 | 0.0 | 100.0 |

RT min: 1.28, wavelength: 220 nm
HPLC Method: SUNFIRE C18 (4.6×150)mm, 3.5 micron
Buffer: 0.05% TFA in water pH 2.5
Mobile Phase A: Buffer:MeCN (95:5)
Mobile Phase B: MeCN:Buffer (95:5)
    Flow: 1 ml/min

| Time | B % |
|---|---|
| 0 | 10 |
| 12 | 100 |
| 15 | 100 |

Wavelength: 254 nm, RT min: 4.796
  Wavelength: 220 nm, RT min: 4.796
Preparative HPLC Method
Column: Symmetry C18 (19×250×70
Mobile Phase: 10 Mm Ammonium acetate (A), MeCN (B)
Gradient:

| Time | Flow | B % |
|---|---|---|
| 0 | 14 ml/min | 10 |
| 15 | 14 ml/min | 40 |

RT: 10.0 min

Preparation of
3-(pyrimidin-2-yl)oxetan-3-amine.Hydrochloride
salt

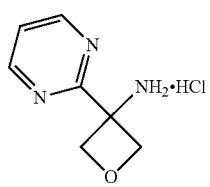

To a yellow solution of 2-methyl-N-(3-(pyrimidin-2-yl) oxetan-3-yl)propane-2-sulfinamide (0.025 g, 0.098 mmol) in MeOH (1 ml) in a 10 ml round-bottomed flask was added a solution of HCl in diethyl ether (0.098 ml, 0.392 mmol, 4N). The reaction mixture was stirred at 0° C. for 10 min., and then concentrated at 25° C. The residue was washed with n-hexane and dried to give the titled product as a white solid (0.017 g, 93%). $^1$H NMR (400 MHz, DMSO-$d_6$): δ 9.15 (bs, 2H), 9.01 (d, J=4.8 Hz, 2H), 7.64 (t, J=5.0 Hz, 1H), 5.00 (d, J=7.2 Hz, 2H), 4.87 (d, J=7.2 Hz, 2H).

Preparation of 4-fluoro-2-(4-fluorophenyl)-N-methyl-5-(2-methyl-5-(3-(pyrimidin-2-yl)oxetan-3-ylcarbamoyl)phenyl)benzofuran-3-carboxamide

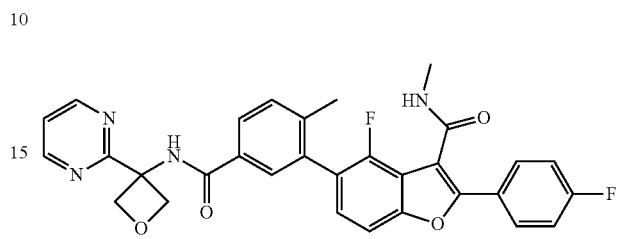

To a yellow solution mixture of 3-(4-fluoro-2-(4-fluorophenyl)-3-(methylcarbamoyl)benzofuran-5-yl)-4-methylbenzoic acid (30 mg, 0.071 mmol) and 3-(pyrimidin-2-yl)oxetan-3-amine hydrochloride (16 mg, 0.085 mmol) in DMF (1 ml) in a 25 ml round-bottomed flask was added benzotriazo-1-yloxytripyrrolidinophosphonium hexafluorophosphate (PyBOP) (50 mg, 0.096 mmol), followed by triethylamine (TEA) (0.1 ml, 0.717 mmol), and the reaction mixture stirred for overnight. Ice cooled water was added to the reaction mixture, which was then stirred for 10-15 min. at 0° C. Precipitation was observed. The solid was collected by filtration, washed with cold water, and then dissolved in dichloromethane. The organic was dried over $Na_2SO_4$, filtered and concentrated. The crude product was purified by preparative HPLC. Yield (12 mg, 30%).

$^1$H NMR (400 MHz, $CD_3OD$): δ 8.84 (d, J=4.8 Hz, 2H), 7.98-7.94 (m, 2H), 7.92 (dd, J=2, 8 Hz, 1H), 7.86 (d, J=2 Hz, 1H), 7.55 (d, J=8.4 Hz, 1H), 7.48 (d, J=8 Hz, 1H), 7.40 (t, J=4.8 Hz, 1H), 7.35-7.27 (dd overlapping with t, 3H), 5.24 (d, J=6.8 Hz, 2H), 5.10 (d, J=6.4 Hz, 2H), 2.96 (s, 3H), 2.31 (s, 3H).

$^{19}$F NMR (376.57 MHz, $CD_3OD$)-112.27, −122.69.
LCMS: (ES+) m/z=555 (M+H)$^+$
Column-XBridege phenyl (4.6×30)mm, 3.5 micron
Mphase A: 2% MeCN—98% $H_2O$—10 mM $NH_4COOH$
Mphase B: 98% MeCN—2% $H_2O$—10 mM $NH_4COOH$
Flow: 1.8 ml/Min

| Time | % A | % B |
|---|---|---|
| 0.0 | 100.0 | 0 |
| 1.5 | 0.0 | 100.0 |
| 3.2 | 0.0 | 100.0 |

RT min: 1.59, wavelength: 220 nm
HPLC Method: XBridege phenyl (4.6×150)mm, 3.5 micron
  Buffer: 0.05% TFA in water pH 2.5
  Mobile Phase A: Buffer:MeCN (95:5)
  Mobile Phase B: MeCN:Buffer (95:5)
  Flow: 1 ml/min

| Time | B % |
|---|---|
| 0 | 10 |
| 12 | 100 |
| 15 | 100 |

Wavelength: 254 nm, RT min: 9.51
Wavelength: 220 nm, RT min: 9.51
HPLC Method: SUNFIRE C18 (4.6×150)mm, 3.5 micron
Buffer: 0.05% TFA in water pH 2.5
Mobile Phase A: Buffer:MeCN (95:5)
Mobile Phase B: MeCN:Buffer (95:5)
Flow: 1 ml/min

| Time | B % |
|---|---|
| 0 | 10 |
| 12 | 100 |
| 15 | 100 |

Wavelength: 254 nm, RT min: 9.69
Wavelength: 220 nm, RT min: 9.69
Preparative HPLC Method
Column: Sunfire C18-OBD(30×250)mm, 10μ.
Mobile Phase: 10 Mm Ammonium acetate (A), MeCN (B)
Gradient:

| Time | Flow | B % |
|---|---|---|
| 0 | 25 ml/min | 20 |
| 5 | 25 ml/min | 50 |
| 10 | 25 ml/min | 70 |
| 15.5 | 25 ml/min | 70 |
| 16 | 25 ml/min | 100 |

RT: 12.589 min

Preparation of 4-fluoro-2-(4-fluorophenyl)-5-(4-methoxy-2-methyl-5-(3-(pyrimidin-2-yl)oxetan-3-ylcarbamoyl)phenyl)-N-methylbenzofuran-3-carboxamide

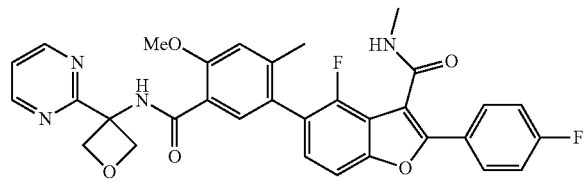 [SMILES: CNC(=O)c1c(-c2ccc(F)cc2)oc2ccc(-c3cc(C(=O)NC4(c5ncccn5)COC4)c(OC)cc3C)c(F)c12]

To a yellow solution mixture of 5-(4-fluoro-2-(4-fluorophenyl)-3-(methylcarbamoyl)benzofuran-5-yl)-2-methoxy-4-methylbenzoic acid (30 mg, 0.066 mmol) and 3-(pyrimidin-2-yl)oxetan-3-amine hydrochloride (12.5 mg, 0.067 mmol) DMF (1 ml) in a 25 ml round-bottomed flask was added PyBOP (50 mg, 0.096 mmol), followed by TEA (0.1 ml, 0.717 mmol), and the reaction mixture stirred for overnight. Ice cooled water was added to the reaction mixture, which was then stirred for 10-15 min. at 0° C. Precipitation was observed. The solid was collected by filtration, washed with cold water, and then dissolved in dichloromethane. The organic solution was dried over $Na_2SO_4$, filtered and concentrated. The crude product was purified by preparative HPLC. Yield (6 mg, 15%).

$^1$H NMR (400 MHz, $CD_3OD$): δ 8.88 (d, J=5.2 Hz, 2H), 7.96-7.93 (m, 2H), 7.85 (s, 1H), 7.50 (d, J=8.4 Hz, 1H), 7.43 (t, J=4.8 Hz, 1H), 7.30-7.24 (overlapping m, 3H), 7.21 (s, 1H), 5.22 (m, 4H), 4.15 (s, 3H), 2.95 (s, 3H), 2.31 (s, 3H).

$^{19}$F NMR (376.57 MHz, $CD_3OD$)-112.35, −122.73.

LCMS: (ES+) m/z=585 $(M+H)^+$
Column-XBridege phenyl (4.6×30)mm, 3.5 micron
Mphase A: 2% MeCN—98% $H_2O$—10 mM $NH_4COOH$
Mphase B: 98% MeCN—2% $H_2O$—10 mM $NH_4COOH$
Flow: 1.8 ml/Min

| Time | % A | % B |
|---|---|---|
| 0.0 | 100.0 | 0 |
| 1.5 | 0.0 | 100.0 |
| 3.2 | 0.0 | 100.0 |

RT min: 1.61, wavelength: 220 nm
HPLC Method: XBridege phenyl (4.6×150)mm, 3.5 micron
Buffer: 0.05% TFA in water pH 2.5
Mobile Phase A: Buffer:MeCN (95:5)
Mobile Phase B: MeCN:Buffer (95:5)
Flow: 1 ml/min

| Time | B % |
|---|---|
| 0 | 10 |
| 12 | 100 |
| 15 | 100 |

Wavelength: 254 nm, RT min: 9.91
Wavelength: 220 nm, RT min: 9.91
HPLC Method: SUNFIRE C18 (4.6×150)mm, 3.5 micron
Buffer: 0.05% TFA in water pH 2.5
Mobile Phase A: Buffer:MeCN (95:5)
Mobile Phase B: MeCN:Buffer (95:5)
Flow: 1 ml/min

| Time | B % |
|---|---|
| 0 | 10 |
| 12 | 100 |
| 15 | 100 |

Wavelength: 254 nm, RT min: 10.39
Wavelength: 220 nm, RT min: 10.39
Preparative HPLC Method
Column: Sunfire C18-OBD(30×250)mm, 10μ.
Mobile Phase: 10 Mm Ammonium acetate (A), MeCN (B)
Gradient:

| Time | Flow | B % |
|---|---|---|
| 0 | 25 ml/min | 20 |
| 5 | 25 ml/min | 50 |
| 10 | 25 ml/min | 70 |

| Time | Flow | B % |
| --- | --- | --- |
| 15 | 25 ml/min | 70 |
| 16 | 25 ml/min | 100 |

RT: 14.19 min

Preparation of 4-fluoro-5-(3-fluoro-2-methyl-5-(3-(pyrimidin-2-yl)oxetan-3-ylcarbamoyl)phenyl)-2-(4-fluorophenyl)-N-methylbenzofuran-3-carboxamide

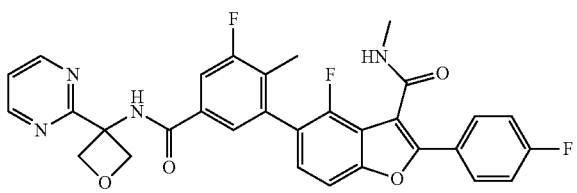 [SMILES: CNC(=O)c1c(-c2ccc(F)cc2)oc2ccc(-c3cc(C(=O)NC4(c5ncccn5)COC4)cc(F)c3C)c(F)c12]

To a yellow solution mixture of 3-fluoro-5-(4-fluoro-2-(4-fluorophenyl)-3-(methylcarbamoyl)benzofuran-5-yl)-4-methylbenzoic acid (30 mg, 0.068 mmol) and 3-(pyrimidin-2-yl)oxetan-3-amine hydrochloride (12.5 mg, 0.067 mmol) in DMF (1 ml) in a 25 mL round-bottomed flask was added PyBOP (50 mg, 0.096 mmol), followed by TEA (0.1 ml, 0.717 mmol), and the reaction mixture was stirred for overnight. Ice cooled water was added to the reaction mixture, which was then stirred for 10-15 min. at 0° C. Precipitation was observed. The solid was collected by filtration, washed with cold water, and then dissolved in dichloromethane. The organic was dried over $Na_2SO_4$, filtered and concentrated. The crude product was purified by preparative HPLC. Yield (10 mg, 25%).

$^1$H NMR (400 MHz, $CD_3OD$): δ 8.84 (d, J=4.8 Hz, 2H), 7.98-7.95 (m, 2H), 7.73-7.71 (overlapping m, 2H), 7.57 (d, J=8.4 Hz, 1H), 7.40 (t, J=4.8 Hz, 1H), 7.41-7.28 (overlapping dd and t, 3H), 5.24 (d, J=6.4 Hz, 2H), 5.09 (d, J=6.4 Hz, 2H), 2.97 (s, 3H), 2.22 (s, 3H).

$^{19}$F NMR (376.57 MHz, $CD_3OD$)-112.14, −116.54, −122.56.

LCMS: (ES+) m/z=573.2 $(M+H)^+$
Column-PUROSPHER@star RP-18 (4×55)mm, 3 μm
Mphase A: 20 mM $NH_4OAc$ in 90% $H_2O$—10% MeCN
Mphase B: 20 mM $NH_4OAc$ in 10% $H_2O$—90% MeCN
Flow: 2.5 ml/Min

| Time | % A | % B |
| --- | --- | --- |
| 0.0 | 100.0 | 0.0 |
| 2.0 | 0.0 | 100.0 |
| 2.5 | 0.0 | 100.0 |
| 3.0 | 100.0 | 0.0 |

RT min: 1.79, wavelength: 220 nm
HPLC Method: XBridege phenyl (4.6×150)mm, 3.5 micron
Buffer: 0.05% TFA in water pH 2.5
Mobile Phase A: Buffer:MeCN (95:5)
Mobile Phase B: MeCN:Buffer (95:5)
Flow: 1 ml/min

| Time | B % |
| --- | --- |
| 0 | 10 |
| 12 | 100 |
| 15 | 100 |

Wavelength: 254 nm, RT min: 9.77
Wavelength: 220 nm, RT min: 9.77
HPLC Method: SUNFIRE C18 (4.6×150)mm, 3.5 micron
Buffer: 0.05% TFA in water pH 2.5
Mobile Phase A: Buffer:MeCN (95:5)
Mobile Phase B: MeCN:Buffer (95:5)
Flow: 1 ml/min

| Time | B % |
| --- | --- |
| 0 | 10 |
| 12 | 100 |
| 15 | 100 |

Wavelength: 254 nm, RT min: 10.25
Wavelength: 220 nm, RT min: 10.25
Preparative HPLC Method
Column: XBridege phenyl C18 (19×100)mm. 7μ
Mobile Phase: 10 Mm Ammonium acetate (A), MeCN (B)
Gradient:

| Time | Flow | B % |
| --- | --- | --- |
| 0 | 12 ml/min | 50 |
| 5 | 12 ml/min | 65 |
| 15 | 12 ml/min | 65 |
| 15.1 | 12 ml/min | 100 |
| 18 | 12 ml/min | 100 |
| 18.1 | 12 ml/min | 50 |
| 22 | 12 ml/min | 50 |

RT: 14.285 min

Synthesis of methyl 2-methoxy-5-(4,4,5,5-tetramethyl-1,3,2-dioxaborolan-2-yl)benzoate Step 1: Preparation of methyl 5-bromo-2-methoxybenzoate

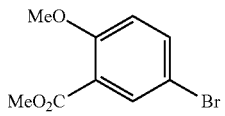

To a mixture of 5-bromo-2-hydroxybenzoic acid (10.0 g, 46.1 mmol) in acetone (100 mL) in a 250 mL round bottom flask was added $K_2CO_3$ (15.90 g, 115 mmol) and then dimethyl sulfate (10.92 mL, 115 mmol). The resulting reaction mixture was stirred at 50° C. for overnight. After completion of reaction, the reaction mixture was filtered and concentrated to get the crude compound, which was then added with water and extracted with diethyl ether (200 mL×2). The combined organic extracts were washed with 10% $NaHCO_3$ solution, dried over $Na_2SO_4$, filtered and evaporated to give a colorless liquid. Yield: 11.7 g (77%).

¹H NMR (400 MHz, CDCl₃) δ: 7.90 (s, 1H), 7.57-7.54 (m, 1H), 6.88-6.86 (s, 1H), 3.89 (s, 6H).
LCMS: (ES+) m/z=245 (M+H)⁺
Column: Acquity HPLC BEH C18 1.7 um, 2.1×50 mm Column
Mobile (M) phase A: 0.1% TFA in water
Mobile (M) phase B: Acetonitrile

| Time (min): | 0 | 1 | 1.6 |
|---|---|---|---|
| % B: | 2% | 98%: | 98% |

Retention Time (RT): 0.92 min

Step 2: Preparation of methyl 2-methoxy-5-(4,4,5,5-tetramethyl-1,3,2-dioxaborolan-2-yl)-benzoate

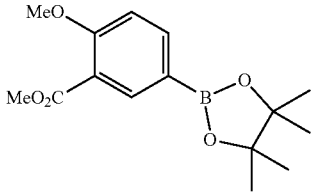 [SMILES: COC(=O)c1cc(B2OC(C)(C)C(C)(C)O2)ccc1OC]

A mixture of methyl 5-bromo-2-methoxybenzoate (4.5 g, 18.36 mmol), KOAc (5.45 g, 55.1 mmol), bis(pinacolato) diboron (5.57 g, 22.03 mmol) in dioxane (40 ml) in a 80 ml microwave reaction vessel was degassed and then added with PdCl₂(dppf) (1.344 g, 1.836 mmol). It was then heated in microwave at 100° C. for 3 hr. After heating was stopped, the reaction mixture was filtered through a cake of celite and then concentrated under vacuum. The crude compound was purified by Combiflash using 15% ethyl acetate/n-hexane as a mobile phase. Yield 3.5 g (67%). 1H NMR (400 MHz, CDCl₃) δ: 8.22 (d, J=1.6 Hz, 1H), 7.91-7.89 (m, 1H), 7.00-6.98 (d, J=8.0 Hz, 1H), 3.93 (s, 3H), 3.88 (s, 3H), 1.34 (s, 12H).
LCMS: (ES+) m/z=294 (mass peak observed)
Column: PUROSPHER@star RP-18 (4×55) mm, 3 μm
Buffer: 20 m MNH₄OAc In WATER
M phase A: Buffer+MeCN (90+10)
M phase B: Buffer+MeCN (10+90)
Flow: 2.5 ml/min

| Time (min.): | 0 | 2 | 2.5 | 3 |
|---|---|---|---|---|
| % B: | 0 | 100 | 100 | 0 |

RT: 1.98 min.

3-(Pyrimidin-2-yl)oxetan-3-amine hydrochloride salt was prepared as described

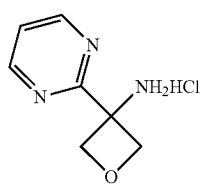

LCMS: (ES+) m/z=152.2 (M+H)⁺
Column-Ascentis Express C8 (5×2.1 mm-2.7 μm)
M phase A: 2% MeCN—98% H₂O—10 mM NH₄COOH
M phase B: 98% MeCN—2% H₂O—10 mM NH₄COOH
Flow=1 mL/min

| Time | 0.0 | 1.5 | 3.2 |
|---|---|---|---|
| % A | 100.0 | 0.0 | 0.0 |
| % B | 0.0 | 100.0 | 100.0 |

Time (min.): RT min: 0.45, wavelength: 220 nm

Preparation of 2-(4-fluorophenyl)-3-(methylcarbamoyl)-6-nitrobenzofuran-5-yl trifluoromethanesulfonate

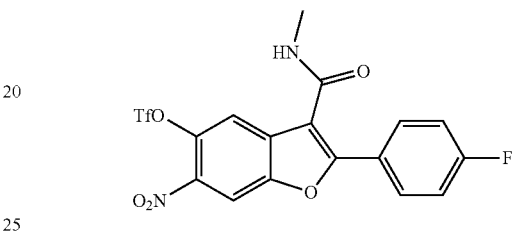

To a mixture of 2-(4-fluorophenyl)-5-hydroxy-N-methyl-6-nitrobenzofuran-3-carboxamide (1.5 g, 4.54 mmol) in pyridine (30 mL) in a pressure tube at room temperature was added DMAP (0.555 g, 4.54 mmol). The reaction mixture was cooled to 0° C. and then added with triflic anhydride (1.151 mL, 6.81 mmol) slowly, warmed to room temperature and then stirred overnight. The reaction mixture was diluted with water and stirred for 10 min. The solid filtered, washed with water and dried under suction. Yield: 1.8 g (86%). ¹H NMR (400 MHz, DMSO-d₆) δ: 8.83 (s, 1H), 8.61 (d, J=4.52 Hz, 1H), 8.05-7.99 (m, 2H), 7.96 (s, 1H), 7.52-7.45 (m, 2H), 2.85 (d, J=4.52 Hz, 3H).
LCMS: (ES−) m/z=461 (M−H)⁻
Column: PUROSPHER@star RP-18 (4×55) mm, 3 μm
Buffer: 20 mM NH₄OAc in WATER
M phase A: Buffer+MeCN (90+10)
M phase B: Buffer+MeCN (10+90)
Flow: 2.5 ml/min

| Time (min.): | 0 | 2 | 2.5 | 3 |
|---|---|---|---|---|
| % B: | 0 | 100 | 100 | 0 |

Time (min.): RT min: 1.98, wavelength: 220 nm

Preparation of methyl 5-(2-(4-fluorophenyl)-3-(methylcarbamoyl)-6-nitrobenzo-furan-5-yl)-2-methoxybenzoate

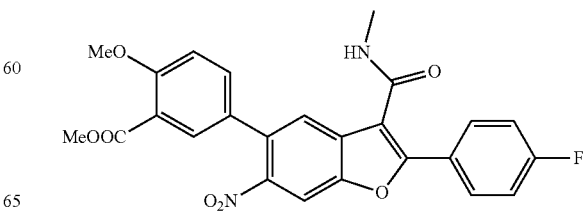

To a mixture of 2-(4-fluorophenyl)-3-(methylcarbamoyl)-6-nitrobenzofuran-5-yl trifluoromethanesulfonate (750 mg, 1.622 mmol), methyl 2-methoxy-5-(4,4,5,5-tetramethyl-1,3,2-dioxaborolan-2-yl)benzoate (569 mg, 1.947 mmol) and cesium carbonate (1057 mg, 3.24 mmol) in dioxane (20 mL)/water (1.0 mL) at rt under nitrogen was added Pd(PPh$_3$)$_4$(0) (187 mg, 0.162 mmol). The reaction mixture was heated to 100° C. and maintained at the same temperature for overnight. The reaction mixture was filtered through celite, and the celite bed washed with ethyl acetate. The filtrate was concentrated and the residue purified by Combiflash using MeOH/CHCl$_3$ as eluant. The desired fraction was collected at 2.5% MeOH in CHCl$_3$. Yield: 0.650 g (83%).

$^1$H NMR (400 MHz, DMSO-d$_6$) δ ppm 8.58 (q, J=4.43 Hz, 1H), 8.52 (s, 1H), 8.11-7.98 (m, 2H), 7.69-7.66 (m, 1H), 7.74-7.62 (m, 1H), 7.58-7.52 (m, 1H), 7.49-7.40 (m, 2H), 7.28 (s, 1H), 3.94-3.86 (s, 3H), 3.84 (br s, 3H), 2.89-2.79 (d, 3H).
LCMS: (ES−) m/z=477 (M−H)$^-$
Column: PUROSPHER@star RP-18 (4×55) mm, 3 μm
Buffer: 20 mM NH$_4$OAc IN WATER
M phase A: Buffer+MeCN (90+10)
M phase B: Buffer+MeCN (10+90)
Flow: 2.5 ml/min

| Time (min.): | 0 | 2 | 2.5 | 3 |
|---|---|---|---|---|
| % B: | 0 | 100 | 100 | 0 |

Time (min.): RT min: 1.90, wavelength: 220 nm

Preparation of 5-(2-(4-fluorophenyl)-3-(methylcarbamoyl)-6-nitrobenzofuran-5-yl)-2-methoxybenzoic acid

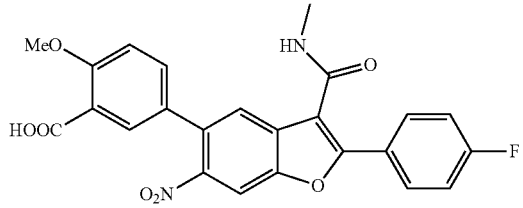 [SMILES: CNC(=O)c1c(-c2ccc(F)cc2)oc2cc([N+](=O)[O-])c(-c3ccc(OC)c(C(=O)O)c3)cc12]

To a solution of methyl 5-(2-(4-fluorophenyl)-3-(methylcarbamoyl)-6-nitrobenzofuran-5-yl)-2-methoxybenzoate (200 mg, 0.418 mmol) in THF (12 mL)/water (4.0 mL) at room temperature was added sodium hydroxide (1.045 mL, 2.090 mmol). The reaction mixture was heated to 50° C. and maintained at the same temperature for overnight. The reaction mixture was concentrated under vacuum to remove the solvent. The residue was diluted with water, acidified with 1.5 N HCl. The solid obtained was filtered and dried under suction. Yield: 175 mg (86%). $^1$H NMR (400 MHz, DMSO-d$_6$) δ ppm 12.81 (br. s, 1H). 8.58 (q, J=4.52 Hz, 1H), 8.49 (s, 1H), 8.08-8.02 (m, 2H), 7.70 (s, 1H), 7.66 (d, J=2.51 Hz, 1H), 7.53 (dd, J=8.66, 2.38 Hz, 1H), 7.49-7.42 (m, 2H), 7.25 (s, 1H), 3.89 (s, 3H), 2.85 (d, J=4.77 Hz, 3H).
LCMS: (ES−) m/z=464 (mass peak observed)
Column-Ascentis Express C8 (5×2.1 mm-2.7 μm)
M phase A: 2% MeCN—98% H$_2$0—10 mM NH$_4$C00H
M phase B: 98% MeCN—2% H$_2$0—10 mM NH$_4$C00H
Flow=1 mL/min

| Time | 0.0 | 1.5 | 3.2 |
|---|---|---|---|
| % A | 100.0 | 0.0 | 0.0 |
| % B | 0.0 | 100.0 | 100.0 |

Time (min.): RT min: 1.78, wavelength: 220 nm

Preparation of 2-(4-fluorophenyl)-5-(4-methoxy-3-((3-(pyrimidin-2-yl)oxetan-3-yl)carbamoyl)phenyl)-N-methyl-6-nitrobenzofuran-3-carboxamide

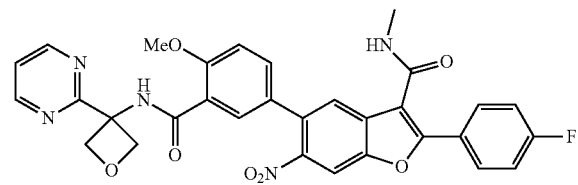 [SMILES: CNC(=O)c1c(-c2ccc(F)cc2)oc2cc([N+](=O)[O-])c(-c3ccc(OC)c(C(=O)NC4(c5ncccn5)COC4)c3)cc12]

To a mixture of 5-(2-(4-fluorophenyl)-3-(methylcarbamoyl)-6-nitrobenzofuran-5-yl)-2-methoxy-benzoic acid (150 mg, 0.323 mmol) and 3-(pyrimidin-2-yl)oxetan-3-amine hydrochloride (77 mg, 0.42 mmol) in DMF at room temperature under a nitrogen atmosphere (7.5 mL) was added triethylamine (0.225 mL, 1.615 mmol). The mixture was cooled to 0° C. and then added with BOP (214 mg, 0.484 mmol) at the same temperature. The reaction mixture was warmed to rt and stirred at rt overnight. The reaction mixture was then diluted with water and stirred for 5 min. The solid obtained was filtered and dried under suction. Yield: 0.180 g (93%).
LCMS: (ES+) m/z=598.2 (M+H)$^+$
Column: PUROSPHER@star RP-18 (4×55)mm, 3 μm
Buffer: 20 mM NH$_4$OAc in WATER
M phase A: Buffer+MeCN(90+10)
M phase B: Buffer+MeCN(10+90)
Flow: 2.5 ml/min

| Time (min.): | 0 | 2 | 2.5 | 3 |
|---|---|---|---|---|
| % B: | 0 | 100 | 100 | 0 |

Time (min.): RT min: 1.76, wavelength: 220 nm

Preparation of 6-amino-2-(4-fluorophenyl)-5-(4-methoxy-3-((3-(pyrimidin-2-yl)-oxetan-3-yl)carbamoyl)phenyl)-N-methylbenzofuran-3-carboxamide

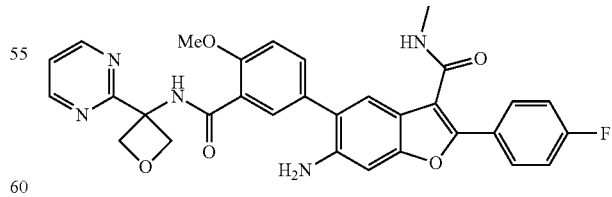

A mixture of 2-(4-fluorophenyl)-5-(4-methoxy-343-(pyrimidin-2-yl)oxetan-3-yl)carbamoyl)phenyl)-N-methyl-6-nitrobenzofuran-3-carboxamide (180 mg, 0.301 mmol) and ammonium chloride (161 mg, 3.01 mmol) in ethanol (10 mL) in a sealed tube at room temperature was stirred for 5 min and then added with indium (173 mg, 1.506 mmol) powder. The reaction mixture was heated to 90° C. and maintained at the same temperature for overnight. The reaction mixture was concentrated, diluted with water and stirred for 5 min. The solid was filtered and dried under suction.

Yield: 120 mg (56.3%).

LCMS: (ES+) m/z=568.2 (M+H)+

Column: PUROSPHER@star RP-18 (4×55)mm, 3 μm

Buffer: 20 mM NH4OAc in WATER

M phase A: Buffer+MeCN(90+10)

M phase B: Buffer+MeCN(10+90)

Flow: 2.5 ml/min

| Time (min.): | 0 | 2 | 2.5 | 3 |
|---|---|---|---|---|
| % B: | 0 | 100 | 100 | 0 |

Time (min.): RT min: 1.61, wavelength: 220 nm

Preparation of 6-(ethylamino)-2-(4-fluorophenyl)-N-methyl-5-(3-(3-(pyrimidin-2-yl)oxetan-3-ylcarbamoyl)phenyl)benzofuran-3-carboxamide

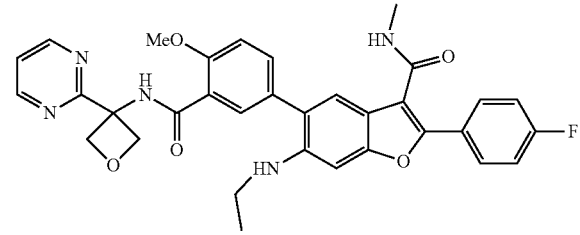 [SMILES: CCNc1cc2oc(-c3ccc(F)cc3)c(C(=O)NC)c2cc1-c1ccc(OC)c(C(=O)NC2(c3ncccn3)COC2)c1]

A mixture of 6-amino-2-(4-fluorophenyl)-5-(4-methoxy-343-(pyrimidin-2-yl)oxetan-3-yl)carbamo-yl)-phenyl)-N-methylbenzofuran-3-carboxamide (100 mg, 0.176 mmol) in MeOH (10 mL) at room temperature was added with acetaldehyde (0.020 mL, 0.352 mmol), stirred for 5 min and then added with sodium cyanoborohydride (22.14 mg, 0.352 mmol). The reaction mixture was stirred at rt for 24 hr. The reaction mixture was concentrated. The residue was added with a 10% NaHCO3 aqueous solution and stirred for 5 min. The solid was filtered and dried under suction. Yield: 90 mg (83%).

LCMS: (ES+) m/z=596.2 (M+H)+

Column: PUROSPHER@star RP-18 (4×55)mm, 3 μm

Buffer: 20 mM NH4OAc IN WATER

M phase A: Buffer+MeCN(90+10)

M phase B: Buffer+MeCN(10+90)

Flow: 2.5 ml/min

| Time (min.): | 0 | 2 | 2.5 | 3 |
|---|---|---|---|---|
| % B: | 0 | 100 | 100 | 0 |

Time (min.): RT min: 1.83, wavelength: 220 nm

Preparation of 6-(N-ethylmethylsulfonamido)-2-(4-fluorophenyl)-N-methyl-5-(3-(3-(pyrimidin-2-yl)oxetan-3-ylcarbamoyl)phenyl)benzofuran-3-carboxamide

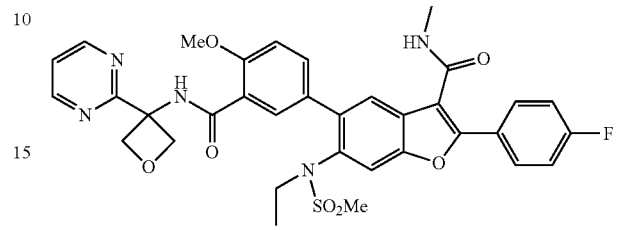

A mixture of 6-(ethylamino)-2-(4-fluorophenyl)-5-(4-methoxy-3-((3-(pyrimidin-2-yl)oxetan-3-yl)carbamoyl)phenyl)-N-methylbenzofuran-3-carboxamide (90 mg, 0.151 mmol), pyridine (5.0 mL), DMAP (18.46 mg, 0.151 mmol) and methanesulfonyl chloride (0.018 mL, 0.227 mmol) was stirred at room temperature overnight. The reaction mixture was diluted with water and extracted with EtOAc (20 ml×2). The combined organic extracts were washed with brine, dried over Na2SO4 and concentrated. The crude product was purified by prep HPLC.

LCMS: (ES+) m/z=674.48 (M+H)+

Mobile phase A: 5 mM Ammonium Acetate:MeCN (95:5)

Mobile phase B: 5 mM Ammonium Acetate:MeCN (5:95)

Method:% B: 0 min—5%; 1.1 min—95%; 1.7 min—95%

RT min: 0.92, wavelength: 220 nm

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

We claim:

1. A compound of formula I

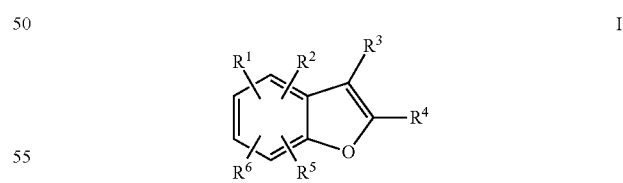

where:

$R^1$ is phenyl or pyridinyl and is substituted with 0-3 substituents selected from the group consisting of halo, alkyl, haloalkyl, hydroxyalkyl, alkoxyalkyl, alkoxy, hydroxyalkyloxy, and alkoxyalkyloxy, and is also substituted with 1 $CON(R^9)(R^{10})$ substituent;

$R^2$ is hydrogen, halo, or alkyl;

$R^3$ is $CONHCH_3$;

$R^4$ is phenyl that is independently substituted with 0-2 halo or methoxy or is para substituted with X—$Ar^1$;

$R^5$ and $R^6$ are independently hydrogen, alkyl, halo, $N(R^7)(R^8)$, or alkylsulfonyl;

$R^7$ and $R^8$ are independently hydrogen, alkyl, hydroxyalkyl, alkoxyalkyl, alkylsulfonyl, or alkylsulfonylalkyl; or $N(R^7)(R^8)$ taken together is azetidinyl, pyrrolidinyl, piperidinyl, or piperazinyl, and is substituted with 0-2 substituents selected from alkyl, hydroxyalkyl, or hydroxy;

$R^9$ is hydrogen;

$R^{10}$ is

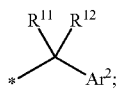

$R^{11}$ and $R^{12}$ taken together is —CH$_2$OCH$_2$—, —OCH$_2$CH$_2$—, —CH$_2$OCH$_2$CH$_2$—, —OCH$_2$CH$_2$CH$_2$—, —OCH$_2$CH$_2$CH$_2$CH$_2$—, —CH$_2$OCH$_2$CH$_2$CH$_2$—, —CH$_2$CH$_2$OCH$_2$CH$_2$— (thus forming an oxetanyl, dihydrofuranyl, or dihydropyranyl ring);

X is —O— or —NH—;

Ar$^1$ is phenyl or para-halophenyl; and

Ar$^2$ is phenyl, pyridinyl, pyrazolyl, isoxazolyl, imidazolyl, oxazolyl, thiazolyl, oxadiazolyl, oxadiathiazolyl, triazolyl, tetrazolyl, pyrazinyl, or pyrimidinyl, and is substituted with 0-3 substituents selected from halo, alkyl, or dialkylamino;

or a pharmaceutically acceptable salt thereof.

2. A compound of claim 1 where $R^1$ is phenyl substituted with 0-2 substituents selected from the group consisting of halo, alkyl, or alkoxy, and is also substituted with 1 CON(R$^9$)(R$^{10}$) substituent;

$R^2$ is hydrogen or fluoro;

$R^3$ is CONHCH$_3$ $R^4$ is phenyl that is para substituted with fluoro;

$R^5$ and $R^6$ are hydrogen;

$R^9$ is hydrogen;

$R^{10}$ is

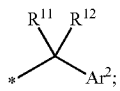

$R^{11}$ and $R^{12}$ taken together is —CH$_2$OCH$_2$— (thus forming an oxetanyl ring); and Ar$^2$ is phenyl, pyridinyl, or pyrimidinyl and is substituted with 0-3 substituents selected from halo or alkyl;

or a pharmaceutically acceptable salt thereof.

3. A compound of claim 2 where $R^1$ is phenyl substituted with 0-2 substituents selected from the group consisting of methyl, fluoro, and methoxy, and is also substituted with 1 CON(R$^9$)(R$^{10}$) substituent; $R^2$ is F; $R^3$ is CONHCH$_3$; $R^5$ and $R^6$ are hydrogen; $R^9$ is hydrogen; $R^{10}$ is

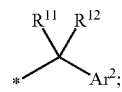

$R^{11}$ and $R^{12}$ taken together is —CH$_2$OCH$_2$—(thus forming an oxetanyl ring); and Ar$^2$ is phenyl, pyridinyl, or pyrimidinyl; or a pharmaceutically acceptable salt thereof.

4. A compound of claim 3 selected from the group consisting of

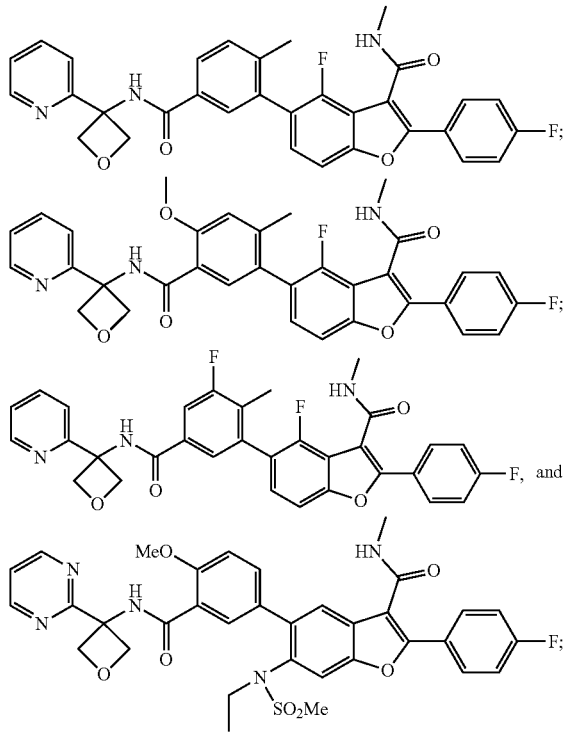

or a pharmaceutically acceptable salt thereof.

5. A composition comprising a compound of claim 1 or a pharmaceutically acceptable salt thereof and a pharmaceutically acceptable carrier.

6. A method of treating hepatitis C infection comprising administering a therapeutically effective amount of a compound of claim 1 to a patient.

* * * * *

UNITED STATES PATENT AND TRADEMARK OFFICE
CERTIFICATE OF CORRECTION

PATENT NO. : 8,507,683 B2  
APPLICATION NO. : 13/310863  
DATED : August 13, 2013  
INVENTOR(S) : Kap-Sun Yeung et al.

Page 1 of 1

It is certified that error appears in the above-identified patent and that said Letters Patent is hereby corrected as shown below:

In the Claims:

Claim 2:

Column 47, line 36, change "CONHCH$_3$" to -- CONHCH$_3$; --.

Signed and Sealed this  
Twenty-ninth Day of April, 2014

Michelle K. Lee  
*Deputy Director of the United States Patent and Trademark Office*